(12) United States Patent
Suzuki et al.

(10) Patent No.: US 7,323,039 B2
(45) Date of Patent: Jan. 29, 2008

(54) METHOD FOR PREPARING MICROSPHERE

(75) Inventors: Takehiko Suzuki, Osaka-fu (JP); Yasuhisa Matsukawa, Osaka (JP); Akira Suzuki, Itami (JP)

(73) Assignee: Mitsubishi Tanabe Pharma Corporation, Osaka-shi (JP)

( * ) Notice: Subject to any disclaimer, the term of this patent is extended or adjusted under 35 U.S.C. 154(b) by 0 days.

(21) Appl. No.: 11/302,217

(22) Filed: Dec. 14, 2005

(65) Prior Publication Data

US 2006/0096715 A1    May 11, 2006

Related U.S. Application Data

(62) Division of application No. 10/258,283, filed as application No. PCT/JP01/03599 on Apr. 26, 2001, now Pat. No. 7,011,776.

(30) Foreign Application Priority Data

Apr. 28, 2000   (JP)  ............................. 2000-130383

(51) Int. Cl.
     *B01D 53/22*    (2006.01)
     *B01D 63/00*    (2006.01)
     *B01D 13/12*    (2006.01)

(52) U.S. Cl. ...................... 96/6; 96/4; 96/10; 210/640; 210/188; 210/651; 210/348; 210/643; 210/321.6; 427/213.3; 428/402.21; 55/385.1

(58) Field of Classification Search ...................... 96/4, 96/6, 10; 95/45, 46, 50; 210/640, 188, 651; 264/4.1, 4.3, 4.33, 4.6; 427/2.14, 213.3, 427/213.32, 213.33, 213.36, 231.33; 428/402.2, 428/402.21
See application file for complete search history.

(56) References Cited

U.S. PATENT DOCUMENTS 5,110,475 A  *  5/1992   Rossling et al. ............ 210/640
5,278,106 A      1/1994   Nakashima et al.

(Continued)

FOREIGN PATENT DOCUMENTS

JP         59022603        2/1984

(Continued)

OTHER PUBLICATIONS

Xianshe Feng et al., Separation of Volatile Organic Compound/Nitrogen Mixtures by Polymeric Membranes, Ind. Eng. Chem. Res. 1993, 32, 533-539.

*Primary Examiner*—Jason M. Greene
(74) *Attorney, Agent, or Firm*—Finnegan, Henderson, Farabow, Garrett & Dunner, L.L.P.

(57) ABSTRACT

It is to provide an improved method for preparation of microsphere from an emulsion wherein an organic phase containing an organic solvent having a boiling point lower than that of water and a hardly-water-soluble polymer is emulsified in an aqueous phase by an in-water drying method, which comprises: (1) using an apparatus equipped with a gas separation membrane; (2) supplying the emulsion to be subjected to in-water drying to one side of said gas separation membrane; (3) evaporating off the organic solvent contained in said emulsion to the other side of said gas separation membrane, which can remove the organic solvent with high efficiency and can be carried out in a closed system and hence is favorable from the environmental viewpoint.

11 Claims, 8 Drawing Sheets

U.S. PATENT DOCUMENTS

| | | | |
|---|---|---|---|
| 5,376,347 A * | 12/1994 | Ipponmatsu et al. | 423/338 |
| 5,603,961 A * | 2/1997 | Suzuki et al. | 424/502 |
| 5,770,631 A | 6/1998 | Fukutomi et al. | |
| 6,075,073 A * | 6/2000 | McGlothlin et al. | 210/640 |
| 6,087,324 A | 7/2000 | Igari et al. | |
| 6,291,013 B1 | 9/2001 | Gibson et al. | |
| 6,364,934 B1 * | 4/2002 | Nandu et al. | 96/6 |
| 6,440,493 B1 | 8/2002 | Gibson et al. | |

FOREIGN PATENT DOCUMENTS

| | | |
|---|---|---|
| JP | 59206059 | 11/1984 |
| JP | 5015749 | 1/1993 |
| JP | 6055166 | 1/1994 |
| JP | 7284641 | 10/1995 |
| JP | 8057274 | 3/1996 |
| JP | 9117642 | 5/1997 |
| JP | 9255590 | 9/1997 |
| JP | 2000281716 | 10/2000 |
| JP | 2001062284 | 3/2001 |
| JP | 2000239152 | 5/2002 |
| WO | WO 99/25319 | 5/1999 |

* cited by examiner

METHOD FOR PREPARING MICROSPHERE

RELATED APPLICATIONS

This application is a divisional of U.S. application Ser. No. 10/258,283 filed Oct. 23, 2002, now U.S. Pat. No. 7,011,776, issued Mar. 14, 2006, which is a 371 of International Application No. PCT/JP01/03599 filed Apr. 26, 2001.

TECHNICAL FIELD

The present invention relates to an improved method for preparation of microsphere by an in-water drying method, more particularly, the present invention relates to a method for preparation of microsphere from an emulsion wherein an organic phase containing an organic solvent having a boiling point lower than that of water and a hardly-water-soluble polymer is emulsified in an aqueous phase by an in-water drying method, which comprises using an apparatus equipped with a gas separation membrane, supplying the emulsion to be subjected to in-water drying to one side of said gas separation membrane, evaporating off the organic solvent to the other side of said gas separation membrane, by which the organic solvent can effectively be removed, particularly said process being able to be carried out in a closed system, and hence being useful for preparation of microsphere on an industrial scale.

BACKGROUND ART

So-called "an in-water drying method" is known as one of the methods for preparation of microsphere, which comprises dispersing an organic phase prepared by dissolving a hardly-water-soluble polymer in a water-immiscible organic solvent having a boiling point lower than that of water in an aqueous phase to prepare an O/W type emulsion, and thereafter removing the organic solvent (cf., for example, JP-B-56-19324; JP-A-63-91325; JP-A-8-151321; Kajeev Jain et al., "Controlled Drug Delivery by Biodegradable Poly (Ester) Devices: Different Preparative Approaches", Drug Development and Industrial pharmacy, vol. 24 (No. 8), pp. 703-727, 1998; JP-A-60-100516; JP-A-62-201816; JP-A-9-221417; and JP-A-6-211648).

This in-water drying method includes a problem of removal of the organic solvent in view of environmental pollution.

For example, it is known a method comprising emulsifying a drug-containing solution of a polymer in methylene chloride in an aqueous phase and then removing the organic solvent by stirring the emulsion as it stands at room temperature for a long period of time (cf., JP-A-9-221417, etc.), but according to this method, the methylene chloride is released in the air through the aqueous phase.

A regulation for prevention of environmental pollution is issued by Kanagawa Prefecture, whereby the concentration of methylene chloride at an exhaust port of a factory is regulated less than 50 ppm (cf., "A Handbook for Proper Use of Chlorocarbons" issued by Chlorocarbon Sanitary Society, 1996), and further organic solvents such as methylene chloride, chloroform are defined as class I chemical substance which shall be well controlled by the industrial companies by "A law in regard to monitor of the discharging amount etc. of specific chemical substances into environment and improvement of control thereof" published on Jul. 13, 1999 as well as by an Order of the Government issued on Mar. 29, 2000.

Accordingly, when organic solvents such as methylene chloride are used on an industrial scale, it is required to treat it by using an apparatus in a closed system so that the discharge thereof into outside shall be well controlled in view of environmental problem.

Moreover, where the produced microspheres are used as a medicament (particularly, parenteral utilization such as injection, depots), it is essential to sterilize in the step of preparation thereof and it is required to prepare the microspheres in a closed system so as to prevent from contamination of microbes outside.

For a method for controlling the discharge of organic solvents, it has been studied to prepare microspheres in a closed system. For example, a method was proposed where the contact area of an outer aqueous phase and a gaseous phase as well as the rate of circulation and stirring speed of an emulsion are controlled and further a gas is blown onto the emulsion in order to increase the moving speed of gas at the surface of the emulsion (cf., JP-A-9-221418).

However, by the method of blowing of gas onto the surface, the surface area of the emulsion to be contacted with the gas is limited, and hence, it is not enough to remove efficiently the organic solvent for practical use, and further it has very low efficiency of the removal of organic solvent so that a large amount of the aqueous phase is required in order to prevent coagulation of the emulsion. Thus, this method has a problem that it is difficult to miniaturize the apparatus for the preparation of microspheres.

On the other hand, it is also proposed to use a polymer membrane for the purpose of disposal of waste water and recovery of vapor of organic solvent (cf., Ind. Eng. Chem. Res., vol. 32, p. 533, 1993), and there have been found some membranes for separation and recovery of chlorine organic solvents (cf, JP-A-5-15749, JP-A-6-55166, JP-A-7-284641, JP-A-8-57274, JP-A-9-117642).

DISCLOSURE OF INVENTION

The present invention is to provide an improved method for the industrial preparation of microspheres by a known in-water drying method, where the removal of the organic solvent, which has been a problem in the past, can be carried out with high efficiency and further can be carried out in a closed system, and hence is favorable from the environmental viewpoint.

The present inventors have found that in a method for preparation of microspheres by an in-water drying method, when an emulsion is treated by using a gas separation membrane and the organic solvent is evaporated off through said gas separation membrane, the desired removal of the organic solvent can effectively be carried out. The present invention has been completed based on these new findings.

That is, the present invention is to provide a method for preparation of microspheres from an emulsion wherein an organic phase containing an organic solvent having a boiling point lower than that of water and a hardly-water-soluble polymer is emulsified in an aqueous phase by an in-water drying method, which comprises: (1) using an apparatus equipped with a gas separation membrane; (2) supplying a part or whole of the emulsion to be subjected to in-water drying to one side of said gas separation membrane; (3) evaporating off the organic solvent contained in said emulsion to the other side of said gas separation membrane.

According to the method of the present invention, since the microspheres can be prepared in a closed system by an in-water drying method, it is advantageously applied to preparation of microspheres, for example, of medicaments, particularly parenteral preparations such as injection preparations, depots, which are essentially required to be prepared substantially under an aseptic condition. Besides, since it can be done in a closed system, there is no problem of releasing of the organic solvent toward outside, and hence, it is advantageous in that there is no problem of environmental pollution.

Moreover, the removal of the organic solvent can be carried out with high efficiency in the method of the present invention so that the desired microspheres can be produced within a very short period of time. It is also advantageous in that undesirable leak of the medicament contained in the organic phase into the aqueous phase is effectively prevented and further that undesirable coagulation of microspheres hardly occur.

In addition, according to the method of the present invention, the removal of organic solvent can be done with a small amount of aqueous phase, and hence, it is possible to miniaturize the apparatus, which can easily be operated in a closed system, and thereby the resistance in stirring of the emulsion, which is a problem for industrialization of the method, can advantageously be minimized. Moreover, the method of the present invention can continuously proceed by circulating the liquid after evaporating off the organic solvent into the emulsion, and hence, the method of the present invention is particularly useful for the preparation of microspheres on an industrial scale.

Figure 1:
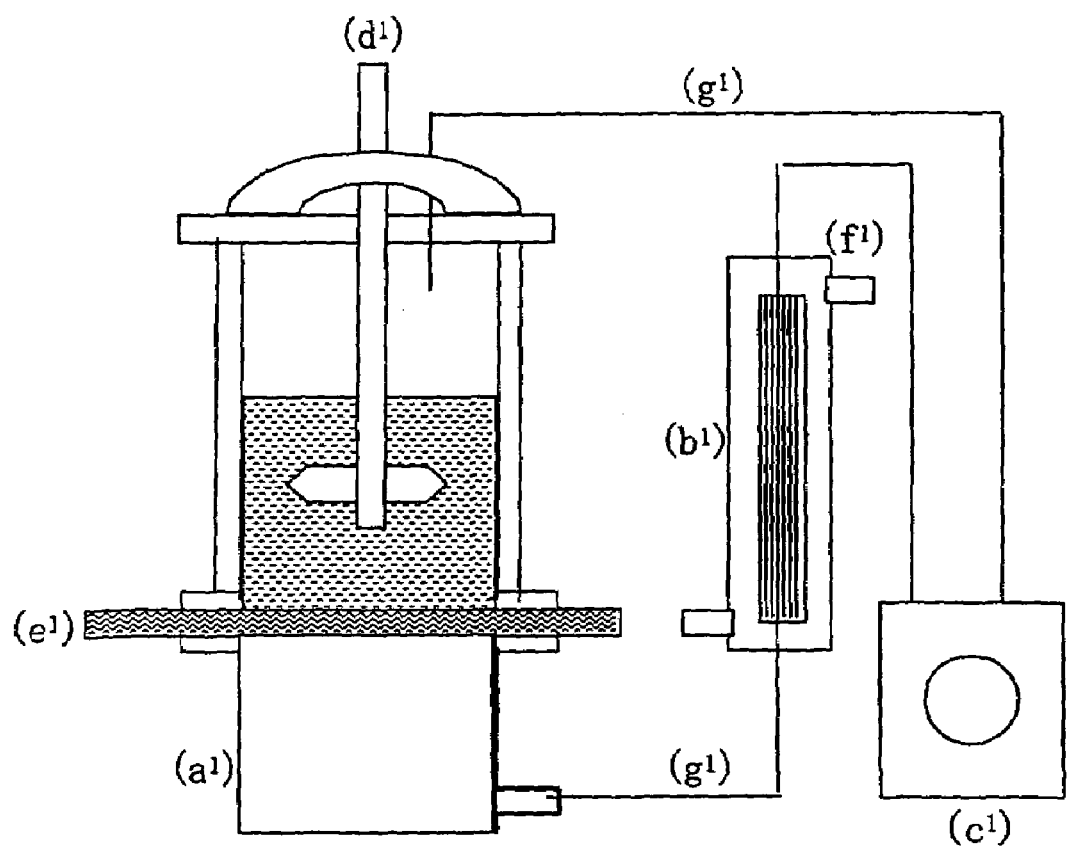
FIG. 1 is a schematic diagram of a circular type of apparatus for producing microspheres.

EXPLANATION OF SYMBOLS $a^1$-$a^5$: A closed vessel
$b^1$, $b^3$: A hollow fiber membrane module
$b^2$, $b^4$, $b^5$: A cylindrical hollow fiber membrane module
$c^1$, $c^3$: A circulating pump
$d^1$, $d^3$, $d^5$: A stirring blade
$d^2$, $d^4$: A magnetic stirring piece
$e^1$, $e^3$: A filter
$f^1$, $f^3$: A ventilation (suction) hole
$f^2$, $f^4$, $f^5$: A pathway for passing a gas
$g^1$, $g^3$: A circulation pathway
$h^2$, $h^4$: A magnetic stirrer $i^3$, $i^4$: A homogenizer
$j^5$: A jacket for controlling temperature

BEST MODE FOR CARRYING OUT THE INVENTION

The emulsion to be applied to the method for preparation of microspheres of the present invention is an O/W type emulsion where an organic phase containing an organic solvent having a boiling point lower than that of water and a hardly-water-soluble polymer is emulsified in an aqueous phase, and when the organic phase contains a medicament, an imaging material (e.g., pigments, colorants) (cf., JP-A-62-95366, JP-A-62-254833, JP-A-6-118636), there can be obtained microspheres containing those materials.

The above "emulsion" can be prepared by various conventional methods depending on the kinds of the organic phase, including the following ones.

(a) An organic phase wherein a medicament, etc. is directly dissolved or dispersed in a solution of a hardly-water soluble polymer, which gives an O/W type emulsion when dispersed into an aqueous phase (cf., JP-B-56-19324, JP-A-63-91325, JP-A-6-32732, JP-A-8-151321, the above-mentioned literature by Jain et al., etc.)

(b) An organic phase of a W/O type emulsion wherein an aqueous solution of a medicament, etc. is dispersed in a solution of a hardly-water soluble polymer, which gives a (W/O)/W type emulsion when dispersed into an aqueous phase (cf., JP-A-60-100516, JP-A-62-201816, JP-A-9-221417, the above-mentioned literature by Jain et al., etc.)

(c) An organic phase of an O/O type emulsion using two or more kinds of hardly-water-soluble polymers wherein a medicament, etc. is dissolved or dispersed in a solution of one hardly-water soluble polymer, which solution is dispersed in a solution of another hardly-water-soluble polymer, which gives an (O/O)/W type emulsion when dispersed into an aqueous phase (cf., JP-A-6-211648) The organic solvent having a boiling point lower than that of water as used in the above methods includes halogenated aliphatic hydrocarbon solvents (e.g., methylene chloride, chloroform, carbon tetrachloride, chloroethane, dichloroethane, trichloroethane, etc.), fatty acid ester solvents (e.g., methyl acetate, ethyl acetate, etc.), aromatic hydrocarbon solvents (e.g., benzene), aliphatic hydrocarbon solvents (e.g., n-hexane, n-pentane, cyclohexane, etc.), ketone solvents (e.g., methyl ethyl ketone, etc.), ether solvents (e.g., diethyl ether, diisopropyl ether, methyl isobutyl ether, methyl tert-butyl ether, tetrahydrofuran, etc.).

These organic solvents have preferably a boiling point of 15-60° C. lower than that of water under the condition of removal of the organic solvents, and particularly preferred organic solvents are methylene chloride, chloroform, and ethyl acetate.

The hardly-water-soluble polymer used in the present method includes various kinds of hardly-water-soluble polymers, but when the microspheres to be prepared are for the purpose of a medicinal use, it is preferably a biodegradable polymer.

The biodegradable polymer includes a polyester of a hydroxyfatty acid and derivatives thereof (e.g., polylactic acid, polyglycolic acid, polycitric acid, polymalic acid, poly-β-hydroxybutyric acid, ε-capro-lactone ring opening polymer, lactic acid-glycolic acid copolymer, 2-hydroxybutyric acid-glycolic acid copolymer, polylactic acid-polyethyleneglycol copolymer, polyglycolic acid-polyethyleneglycol copolymer, etc.), a polymer of an alkyl α-cyanoacrylate (e.g., poly(butyl 2-cyanoacrylate), etc.), a polyalkylene oxalate (e.g., polytrimethylene oxalate, polytetramethylene oxalate, etc.), a polyortho ester, a polycarbonate (e.g., polyethylene carbonate, polyethylenepropylene carbonate, etc.), a polyortho-carbonate, a polyamino acid (e.g., poly-γ-L-alanine, poly-γ-benzyl-L-glutamic acid, poly-γ-methyl-L-glutamic acid, etc.), a hyaluronic acid ester, and the like, and one or more of these polymers can be used.

Among these polymers, particularly preferred ones are polyesters of hydroxyfatty acids, which have an average molecular weight of 2,000 to about 800,000, more preferably 2,000 to about 200,000.

Among the above polyesters of hydroxyfatty acids, more preferable ones are polylactic acid, lactic acid-glycolic acid copolymer, 2-hydroxybutyric acid-glycol acid copolymer. The lactic acid-glycolic acid copolymer has preferably a molar ratio of lactic acid/glycolic acid in the range of 90/10 to 30/70, more preferably 80/20 to 40/60, and the 2-hydroxybutyric acid-glycolic acid copolymer has preferably a molar ratio of 2-hydroxybutyric acid/glycolic acid in the range of 90/10 to 30/70, more preferably 80/20 to 40/60.

The above hardly-water-soluble polymer is dissolved in an organic solvent in a concentration in the organic phase of 0.01 to 90% by weight, preferably 0.1 to 70% by weight.

The O/W type emulsion to be used in the in-water drying method of the present invention can be prepared by mixing a solution of the above hardly-water-soluble polymer in an organic solvent (an organic phase) with water (an aqueous phase) and then emulsifying the mixture. The preparation may be carried out by adding the organic phase to the aqueous phase at one time and then emulsifying the resulting mixture, or alternatively by adding the organic phase to a small portion of the aqueous phase, emulsifying the mixture, and further adding the remaining aqueous phase to the resulting emulsion.

The above emulsifying procedure can easily be carried out by a conventional method, for example, by mixing the organic phase and the aqueous phase with stirring by using a known emulsifying apparatus such as a propeller stirrer, a turbine impeller mixer, a high-pressure emulsifier, an ultrasonic dispersion mixer, a static mixer, etc. Besides, the emulsification may also be done by other methods such as a membrane emulsifying method, a spraying method.

The emulsification by a membrane emulsifying method may be carried out by providing a porous membrane (e.g., porous ceramics which surface is optionally chemically modified, porous glass, etc.) between the organic phase and the aqueous phase, extruding the organic phase into the aqueous phase through fine holes of the porous membrane by giving a pressure to the polymer solution, if necessary with stirring the aqueous phase, for example, by a method as disclosed in Journal of Microencapsulation, vol. 11 (2), pp. 171-178, 1994.

Besides, the emulsification by a spraying method may be carried out by spraying the organic phase onto the aqueous phase with a conventional spraying apparatus. In this method, if necessary, the aqueous phase may be stirred. The spraying apparatus includes, for example, an air nozzle, a pressure nozzle, an ultrasonic nozzle, a rotary atomizer, etc.

The emulsion thus prepared contains the organic phase and the aqueous phase wherein the aqueous phase is in the ratio of 1 to 10,000 parts by volume, preferably 2 to 1,000 parts by volume, per. 1 part by volume of the organic phase.

In the preparation of the above emulsion, an emulsifier may optionally be added to the aqueous phase in order to stabilize the emulsion. The emulsifier includes, for example, an anionic surfactant (e.g., sodium oleate, sodium stearate, sodium laurylsulfate. etc.), a nonionic surfactant (e.g., polyoxyethylene sorbitan fatty acid esters (e.g., Tween 80, Tween 60, manufactured by Nikko Chemicals Co., Ltd.), polyethylene castor oil derivatives (e.g., HCO-60, HCO-50, manufactured by Nikko Chemicals Co., Ltd.), polyvinylpyrrolidone, polyvinyl alcohol, carboxymethyl cellulose, methyl cellulose, lecithin, gelatin, etc.).

The emulsifier is added to the above aqueous phase in an amount of 0.001 to 20% by weight, preferably 0.01 to 10% by weight.

When the organic phase in the emulsion contains a medicament or an imaging material (e.g., pigments, colorants, etc.), etc., there can be obtained microspheres containing such a medicament, etc. These medicaments etc. may be added in an amount of 0.01 to 60% by weight, preferably 0.1 to 40% by weight, more preferably 1 to 30% by weight, based on the weight of the hardly-water-soluble polymer.

Besides, for preparing microspheres containing a medicament, etc., those medicament, etc. may previously be pulverized in order to improving the rate of uptake thereof into the microspheres, which may vary depending on the kinds of the polymer and the solvent to be used, etc. Moreover, when the medicament, etc. form a salt and hence the rate of uptake thereof into the microspheres is low, they may first be converted into a free form and then be subjected to the preparation of microspheres.

The pulverization of the above medicaments, etc. may optionally be carried out by a conventional pulverization method, that is, may physically be pulverized with jet-mill, hammer mill, rotary ball-mill, vibratory ball-mill, beads mill, shaker mill, rod mill, tube mill, etc., or by wet pulverization under a high pressure, or alternatively, by crystallization, for example, by dissolving first the medicament, etc. in a solvent, precipitating them by means of regulating the pH, changing the temperature, components of solvents, etc. and then recovering them by centrifugation or filtration.

The medicaments to be applied to the present invention include various kinds of medicaments, such as antitumor agents, physiologically active peptides, antibiotics, antipyretics, analgesics, antiinflammatories, antitussives, expectorants, sedatives, muscle relaxants, antiepileptics, antiulcers, antidepressants, antiallergic agents, cardiotonics, antiarrythmic agents, vasodilators, antihypertensive diuretics, antidiabetics, antihyperlipidemic agents, anticoagulants, hemostatics, antitubercular agents, hormones, antinarcotic agents, bone resorption inhibitors, promoters of osteogenesis, antiangiogenetics, antiemetics, vitamins, etc. Specific examples of these medicaments are listed below.

Antitumor agents: taxol, bleomycin, methotrexate, actinomycin D, mitomycin C, vinblastine sulfate, vincristine sulfate, daunorubicin, adriamycin, neocercinostatin, cytosine arabinoside, fluorouracil, tetrahydrofuryl-5-fluorouracil, krestin, picibanil, lentinan, tamoxifen, levamisole, bestatin, azimexon, glycyrrhizin, cisplatin, carboplatin, etc.

Physiologically active peptides: insulin, somatostatin, sandostatin, growth hormone, prolactin, adrenocortical tropic hormone (ACTH), ACTH derivatives, melanocyte stimulating hormone (MSH), thyrotrophin releasing hormone (TRH) and its derivatives (e.g., taltirelin, etc.), thyroid stimulating hormone (TSH), luteinizing hormone (LH), luteinizing hormone releasing hormone (LHRH) and its derivatives (e.g., leuprorelin acetate, etc.), follicle stimulating hormone (FSH), vasopressin, desmopressin, oxytocin, calcitonin, elcatonin, parathyroid hormone (PTH), glucagons, gastrin, secretin, pancreozymin, cholecystokinin, angiotensin, human placental lactogen, human chorionic gonadotropin (HCG), enkephalin, enkephalin derivatives, endorphin, kyotorphin, interferons (e.g., α-, β-, γ-, etc.), interleukins (e.g., 1, 2, 3, 4, 5, 6, 7, 8, 9, 10, 11, 12, etc.), taftsin, thymopoietin, thymosin, thymostimulin, thymic humoral factor (THF), serum thymic factor (FTS) and its derivatives, and other thymic factors, tumor necrosis factor (TNF), colony stimulating factors (e.g., CSF, GCSF, GMCSF, MCSF, etc.), motilin, dinorphin, bombesin, neurotensin, cerulein, bradykinin, urokinase, asparaginase, kallikrein, substance P, insulin-like growth factor (IGF-I, IGF-II), nerve growth factor (NGF), cell growth factors (e.g., EGF, TGF-α, TGF-β, PDGF, FGF hydrochloride, basic FGF, etc.), bone morphogenetic protein (BMP), neurotrophic factors (e.g., NT-3, NT-4, CNTF, GDNF, BDNF, etc.), blood coagulation factors VIII and IX, lysozyme chloride, polymixin B, colistin, gramicidin, bacitracin, erythropoietin (EPO), thrombopoietin (TPO), etc.

Antibiotics: gentamycin, dibekacin, kanendomycin, lividomycin, tobramycin, amikacin, fradiomycin, sisomicin, tetracycline hydro-chloride, oxytetracycline hydrochloride, rolitetracycline, doxycycline hydrochloride, ampicillin, piperacillin, ticarcillin, cephalothin, cephaloridine, cefotiam, cefsulodin, cefinenoxime, cefinethazole, cefazolin, cefotaxime, cefoperazone, ceftizoxime, moxolactam, thienamycin, sulfazecin, azthreonam, etc.

Antipyretics, analgesics and anti-inflammatory agents: 5-amino-salicylic acid, salicylic acid, sulpyrine, flufenamic acid, diclofenac, indomethacin, morphine, pethidine hydrochloride, levorphanol tartrate, oxymorphone, etc.

Antitussives and expectorants: ephedrine hydrochloride, methylephedrine hydrochloride, noscapine hydrochloride, codeine phosphate, dihydrocodeine phosphate, alloclamide hydrochloride, chlophedianol hydrochloride, picoperidamine hydrochloride, cloperastine, protokyrol hydrochloride, isoproterenol hydrochloride, salbutamol sulfate, terbutaline sulfate, etc.

Sedatives: chlorpromazine, prochlorperazine, trifluoperazine, atropine sulfate, methyscopolamine bromide, etc.

Muscle relaxants: pridinol methanesulfonate, tubocurarine chloride, pancuronium bromide, etc.

Antiepileptics: phenyloin, ethosuximide, sodium acetazolamide, chlordiazepoxide, etc.

Antiulcers: metoclopramide, histidine hydrochloride, enprostil, etc.

Antidepressants: imipramine, clomipramine, noxiptiline, phenelzine sulfate, etc.

Antiallergic agents: diphenhydramine hydrochloride, chlorpheniramine maleate, tripelenamine hydrochloride, methdilazine hydrochloride, clemizol hydrochloride, diphenylpyraline hydrochloride, methoxyphenamine hydrochloride, etc.

Cardiotonics: trans-π-oxocamphor, theophylol, aminophylline, etilefrine hydrochloride, denopamine, etc.

Anti-arrythmia agents: propranolol, alprenolol, bufetorol, oxyprenolol, azimilide, etc.

Vasodilators: oxyfedrine hydrochloride, diltiazem hydrochloride, tolazoline hydrochloride, hexobendine, bamethan sulfate, etc.

Antihypertensive diuretics: hexamethonium bromide, pentrilium, mecamylamine hydrochloride, ecarazine hydrochloride, clonidine, etc.

Antidiabetics: glymidine sodium, glypizide, phenformin hydro-chloride, buformin hydrochloride, metformin, etc.

Anti-hyperlipidemic agents: pravastatin sodium, simvastatin, clinofibrate, clofibrate, simfibrate, bezafibrate, etc.

Anticoagulants: heparin sodium, etc.

Hemostatics: thromboplastin, thrombin, menadione sodium bisulfite, acetomenaphthone, ε-aminocaproic acid, tranexamic acid, carbazochrome sodium sulfonate, adrenochrome monoaminoguanidine methanesulfonate, etc.

Anti-tubercular agents: isoniazide, ethambutol, p-aminosalicylic acid, etc.

Hormones: prednisolone, prednisolone sodium phosphate, dexamethasone sodium hydrochloride, hexestrol phosphate, methimazole, estrone, etc.

Antinarcotic agents: levallorphan tartrate, nalorphine hydrochloride, naloxone hydrochloride, etc.

Bone resorption inhibitors: ipriflavone, etc.

Promoters of osteogenesis: polypeptides such as BMP, PTH, TGF-β, IGF-I, etc.

Antiangiogenetics: Angiogenesis suppressing steroids, fumagillin, fumagillol derivatives, etc.

Antiemetics: 5-hydroxytryptamine type 3 receptor antagonists such as ondansetron or tropisetron, etc., neurokinin 1 receptor antagonists, etc.

Vitamins: vitamin A, β-carotene, vitamin $B_1$, vitamin $B_2$, niacin, nicotinamide, pantothenic acid, calcium pantothenate, vitamin $B_6$, vitamin $B_{12}$, folic acid, inositol, para-aminohippuric acid, biotin, vitamin C, vitamin D, vitamin E, vitamin K, etc.

The medicaments referred to the above may be in free form or be in a pharmaceutically acceptable salt form. For example, when the medicament possesses a basic group such as an amino group, etc., it may be used in the form of a salt with an inorganic acid (e.g., hydrochloric acid, sulfuric acid, nitric acid, etc.) or with an organic acid (e.g., carbonic acid, succinic acid, etc.). When the medicament possesses an acidic group such as a carboxyl group, it may be used in the form of a salt with an inorganic base (e.g., alkali metals such as sodium, potassium, etc.) or with an organic base (e.g., organic amines such as triethylamine, basic amino acids such as arginine, etc.).

The evaporation of the organic solvent through the gas separation membrane of the present invention is carried out by either one or a combination of two or more of the following methods:

(1) a method of passing a gas on one side of the gas separation membrane which is opposite side of supplying the emulsion ("other side", hereinafter, referred to as merely "the opposite side of emulsion");

(2) a method of decompressing said opposite side of emulsion of the gas separation membrane; or (3) a method of warming the emulsion which is supplied to one side of the gas separation membrane (hereinafter, referred to as merely "the side of emulsion").

In any method, it is preferable to evaporate the organic solvent without exposing the emulsion to the outside air in view of keeping an aseptic condition and of preventing releasing of the organic solvent toward outside.

These methods for evaporation of organic solvent are explained in more detail below.

(1) A Method of Passing a Gas on the Opposite Side of Emulsion of the Gas Separation Membrane:

The passing of a gas may be carried out by any conventional method such as blowing, suction, etc. and the gas to be passed through includes air, nitrogen gas, helium gas, argon gas, etc. When microspheres for medicinal use are prepared, it is preferable to use sterilized and dust-free (filtered) gas.

The rate of passing a gas is usually not less than 0.8 liter/minute, preferably not less than 6.7 liters/minute, per 1 $m^2$ of the membrane area.

(2) A Method of Decompressing the Opposite Side of Emulsion of the Gas Separation Membrane:

The decompressing is carried out with a decompressing pump, a water-air pump, etc., and the decompressing is carried out so that the difference of pressure between the side of emulsion and said opposite side of emulsion is in the range of 1-100 kPa, preferably 20-100 kPa. It is preferable to control in a manner wherein the side of emulsion is normal pressure and the opposite side of emulsion becomes reduced pressure.

(3) A Method of Warming the Side of Emulsion:

The warming is carried out by using a thermostat, an outer bath, a steam bath, etc. so that the emulsion is kept at a prescribed temperature. The preferred range of temperature may vary depending on correlation with a pressure, but it is preferably set at a temperature of not lower than a boiling point of the organic solvent under the pressure at the opposite side of emulsion, and the temperature is usually in the range of 30 to 80° C., preferably 40 to 60° C., while it may vary depending on the kinds of the solvent.

Besides, in any method of the above, in order to remove effectively the organic solvent from the emulsion, it is preferable to stir the emulsion by a conventional stirring means, such as a screw type, a magnetic stirrer type, or a paddle type.

The evaporation of organic solvent by the above methods is preferably done until the content of the organic solvent in the microspheres become 35000 ppm or lower. When methylene chloride is used as an organic solvent, the preparation shall have a final remaining content of the solvent of not more than 600 ppm (cf., a Guideline for Remaining Solvent of Medicaments according to International Conference on Harmonization of Technical Requirements for Registration of Pharmaceuticals for Human Use among Japan, U.S.A. and Europe (ICH)), but the organic solvent may further be removed by treatment after producing the microspheres.

The gas separation membrane used for the evaporation of the above organic solvent in the method of the present invention includes a pervaporation membrane or a porous membrane as mentioned below.

(1) A Pervaporation Membrane

It is a non-porous membrane (a homogeneous membrane) which is effective to separation of a gas taking advantage of the difference in the dissolution rate of the gaseous molecule in the membrane and the rate of diffusion thereof into the membrane. The examples thereof are a silicon-rubber pervaporation membrane (particularly a pervaporation membrane made of polydimethylsiloxane), a membrane prepared by filling silicon rubber into porous polytetrafluoroethylene (cf., JP-A-5-15749), a polyvinyl alcohol mixed membrane (cf., Chemical Engineering, March 1998, pp. 25-29). The membranes may be used in a size of 0.1 to 10,000 $m^2$, preferably 10 to 5,000 $m^2$, per 1 $m^3$ of the aqueous phase.

(2) A Porous Membrane

This membrane is suitable for separation of the organic solvent by utilizing the difference in the flowing rates of the gas molecules within the porous membrane. The examples are a hydrophobic porous membrane made of polytetrafluoroethylene or polypropylene (cf., Journal of Chemical Engineering of Japan, vol. 31, no. 1, pp. 153-156, 1998), a hollow fiber membrane of ionized crosslinked chitosan/polyacrylonitrile composite (cf., Journal of Chemical Engineering of Japan, vol. 25, no. 1, pp. 17-21, 1992). The membranes may be used in a size of 0.1 to 10,000 $m^2$, preferably 10 to 5,000 $m^2$, per 1 $m^3$ of the aqueous phase.

In the method of the present invention, both of the above-mentioned pervaporation membrane and porous membrane can be used, but the pervaporation membrane is preferable in order to keep an sterile condition with a closed vessel and to prevent invasion of outside microbes through the membrane.

Besides, by the treatment of emulsion with these gas separation membrane, it is preferable to set so that the permeation rate of the organic solvent through the membrane is larger than the rate of water, but the organic solvent has a boiling point lower than that of water, and hence, when a temperature is appropriately controlled, the organic solvent can selectively be removed in spite of the permeation rate of the gas separation membrane.

The evaporation of the organic solvent with the above gas separation membrane can be done by various types of methods as mentioned below.

(1) Circulation Type:

A portion of the emulsion is led to one side of the gas separation membrane, to which the evaporation treatment of the organic solvent is applied, and after removal of the organic solvent, the resulting liquid is circulatory returned to the emulsion. In this process, the gas separation membrane is used in the form of a bundle of plural gas separation membranes which form hollow fibers, in order to enlarge the surface area. It is preferable to introduce the emulsion into the inner side of the gas separation membrane in the form of hollow fibers.

Suitable examples of the circular type gas separation membrane are a silicone membrane module ("NAGASEP" manufactured by Nagayanagi Kogyo Kabushiki Kaisha), a deaerating membrane element (SG-100 series, manufactured by Toray Industries, Inc.), a high performance deaerating membrane element (SG-100 series, manufactured by Toray Industries, Inc.), a triple layer composite hollow fibers membrane (a deaerating membrane module, manufactured by Mitsubishi Rayon Co., Ltd.), a hollow fiber membrane module ("SEPAREL", manufactured by Dainippon Ink and Chemicals Inc.).

The circulation of the liquid to be treated is usually carried out by using a circulation pump in the following manner.

(a) A Method of Circulating which Comprises Taking Only a Portion of the Aqueous Phase of the Emulsion as a Portion of the Emulsion A portion of the aqueous phase of the emulsion may be carried out by passing the emulsion through a filter (e.g., a stainless mesh filter, a glass filter, a ceramic filter), or by utilizing the difference of specific gravity between the organic phase and the aqueous phase by using an up-and-down liquid-liquid counterflow apparatus (utilizing an extractor manufactured by Tokyo Rikakikai Co., Ltd.). Among these methods, a method of passing through a filter is preferably used in case of less deformability in the organic phase of the emulsion. This method comprises circulating a portion of the aqueous phase and hence, it can favorably be passed through into the inner side of the hollow fiber gas separation membrane having a smaller diameter of the hollow without clogging of the hollow fiber gas separation membrane.

(b) A Method of Circulating in the State of an Emulsion

This method comprises circulating a portion of the emulsion after subjecting to the evaporation of the organic solvent, where the organic phase of the emulsion contacts the gas separation membrane, and hence, the kinds of the gas separation membrane shall be selected so as to make it fit to the kind of the organic phase.

Besides, when a portion of the emulsion is introduced into the inner side of the hollow fiber gas separation membrane, a suitable size of the hollow fibers of the hollow fiber gas separation membrane shall be selected in order to prevent the clogging, and in this case, it is preferable to decompress the opposite side of emulsion of the gas separation membrane or to warm the emulsion to be provided into the one side of the gas separation membrane.

The method of removal of the organic solvent in the circulation type can be carried out with an apparatus comprising the following basic elements, and the vessel for filling the emulsion may optionally be equipped with a filter, an up-and-down liquid-liquid counterflow apparatus.

(i) a vessel for filling an emulsion;
(ii) a gas separation membrane module for evaporating off an organic solvent from the emulsion;
(iii) a circulation pathway which connects the vessel and the gas separation membrane module; and
(iv) a pump for circulating the emulsion through the gas separation membrane module.

(2) Immersing Type:

This method comprises immersing an emulsion in a tubular gas separation membrane, wherein a gas is passed into the inside of the tube.

It is preferable that the tubular gas separation membrane is in the form of bundles of plural gas membrane which form hollow fibers and have a smaller diameter of the tube in order to increase the surface area, and that the bundle is immersed in the emulsion and a gas is passed into the inner side of the tubular gas separation membrane.

In this method, the organic phase of the emulsion contacts the gas separation membrane, and hence, the kinds of the gas separation membrane shall be selected so as to make it fit to the kind of the organic phase.

The separation membrane is basically the same as the above circular type of membrane. However, when the emulsion is stirred for contacting the emulsion to the gas separation membrane, it is preferable to use a bundle of hollow fiber separation membranes which are figured in a plate or cylindrical shape.

The method of removal of the organic solvent with the immersing type of gas separation membrane is carried out by using an apparatus comprising basically the following elements:

(i) a vessel for filling an emulsion; and
(ii) a gas separation membrane module to be immersed in the emulsion in the vessel for evaporating off an organic solvent from the emulsion.

(3) Channel Type:

According to this type of method, the microspheres are prepared by evaporating the organic solvent at the step of passing the emulsion through a pathway by (a) flowing the emulsion to the outside of the gas separation membrane where a tubular gas separation membrane is arranged within the pathway and passing a gas through the inner side of the tubular gas separation membrane in the direction counter to the flow of the emulsion, or (b) flowing the emulsion the inner side of the gas separation membrane where a tubular gas separation membrane is arranged within the pathway and passing a gas through the outside of the gas separation membrane in the direction counter to the flow of the emulsion.

According to this method, the microspheres can continuously be produced without doing each time (batch system) the operations of filling of the emulsion into a vessel, removal of the organic solvent and thereafter collecting the microspheres from the vessel in contrast to the circulation type of method or the immersing type of method.

The apparatus to be used in the process of the present invention can be designed appropriately so as to make it fit to the various types of gas separation membranes but is not limited to any specific one, but a preferred one is illustrated in the working examples hereinafter.

The organic solvent to be evaporated as mentioned above may preferably be recovered and re-used. The recovering is done by a method of liquefying it by cooling, a method of introducing into a cold water, or a method of adsorbing into porous particles. The adsorbing method is done with an apparatus of adsorbing with fibrous active carbon, a general purpose apparatus of recovering chlorocarbon exhaust gas, a small type of apparatus of recovering chlorocarbon exhaust gas, an apparatus of recovering a low concentration of chlorocarbon exhaust gas, an apparatus of adsorbing with granular active carbon, a fluidized bed apparatus of adsorbing with spherical active carbon, an apparatus of compression and condensation by deeply cooling (cf., Handbook for use of chlorocarbon, pp. 85-93). More specifically, there are used commercially available apparatuses such as an apparatus of recovering and deodorizing of solvent "Ameig" manufactured by Kurimoto Ltd. and an apparatus for adsorbing and condensing a gas of a solvent in low concentration "Haloneater" manufactured by Toyobo Co., Ltd.

The microspheres prepared by the process of the present invention are separated and recovered from the emulsion after evaporation of the organic solvent by a conventional method such as centrifugation, filtering, or screening.

Moreover, when the microspheres are heated over the boiling point of the organic solvent in an aqueous phase (cf., JP Application No. 11-39599) or dried with heating after covering with an additive having a high melting point (cf., JP-A-9-221417), the remaining organic solvent can be removed.

The microspheres thus obtained are further washed to remove the additives of the aqueous phase, etc. which are adhered on the surface, and adding an agglomeration preventing agent such as saccharides, sugar alcohols, inorganic bases, preferably mannitol, sorbitol, in order to prevent the agglomeration among the microspheres, and then subjected to lyophilization.

Moreover, in order to obtain microspheres having the desired particle size, the product is preferably subjected to screening, for example a screen of 1,000 µm or lower. Particularly, the microspheres are used as an injection preparation, the microspheres are preferably passed through a screen of 150 µm or lower in order to easily pass through the needle.

The microspheres prepared by the method of the present invention may be incorporated with medicaments, imaging materials (e.g., pigment, colorant) by adding these medicaments, imaging materials into the organic phas during the preparation of the microspheres, and hence, can be used for medicaments, non-carbon papers, aqueous ink, or the like by selecting the additives.

In case of microspheres containing medicaments, they may be in the form of fine granules, suspensions, embedded type preparations, injections, preparations applying to the skin, and can be administered orally or parenterally [intramuscular injection, subcutaneous injection, administration into blood vessel, percutaneous administration, administration via viscous membrane (per oral cavity, per vaginal administration, per rectal administration, etc.)].

When the medicament-containing microspheres are used as an injection preparation or a suspension preparation (e.g., dry syrup for oral administration), they may preferably be prepared in the form of a liquid preparation by incorporating a dispersing agent (e.g., nonionic surfactants, polyethylene castor oil derivatives, cellulose thickeners), or alternatively, they may be dispersed in water by adding the dispersing agent as mentioned above and an excipient (e.g., mannitol, sorbitol, lactose, glucose, xylitol, maltose, galactose, sucrose), and solidified by lyophilization, drying under reduced pressure, spray drying, etc., and the solidified preparation is dissolved in distilled water for injection when used.

The above injection preparation may further optionally be incorporated by preservatives (e.g., methylparaben, propylparaben, benzyl alcohol, chlorobutanol, sorbic acid, boric acid, etc.), isotonic agents (e.g., sodium chloride, glycerin, sorbitol, glucose, etc.), pH adjustors (e.g., sodium hydroxide, potassium hydroxide, hydrochloric acid, phosphoric acid, citric acid, oxalic acid, carbonic acid, acetic acid, arginine, lysine, etc.).

EXAMPLES

The present invention is illustrated by the following Examples, Comparative Examples, Experiments, but should not be construed to be limited thereto.

Example of Apparatuses

The apparatuses, which may be used for preparing microspheres of the present invention are illustrated in FIG. 1 to FIG. 5.

In order to prepare the microspheres by using the apparatus as shown in FIG. 1, the emulsion to be subjected to an in-water drying is filled in a closed vessel ($a^1$), and a portion of the aqueous phase of the emulsion passed through a filter ($e^1$) (e.g., a stainless mesh) provided at the middle of the closed vessel ($a^1$) is circulated with stirring with a stirring blade ($d^1$) by passing through a hollow fiber membrane module by the use of a circulation pump ($c^1$) via a circulation pathway ($g^1$) made of a silicone rubber, etc. During the circulation, when the portion of the aqueous phase is passed through the hollow fiber membrane module, the organic solvent contained therein is passed and permeated through the hollow fiber membrane and is evaporated through the ventilation (or suction) hole ($f^1$) and thereby the organic solvent can be efficiently evaporated off to out of the system, and thereby the microspheres are formed above the filter ($e^1$) provided in the closed vessel ($a^1$).

Figure 2:
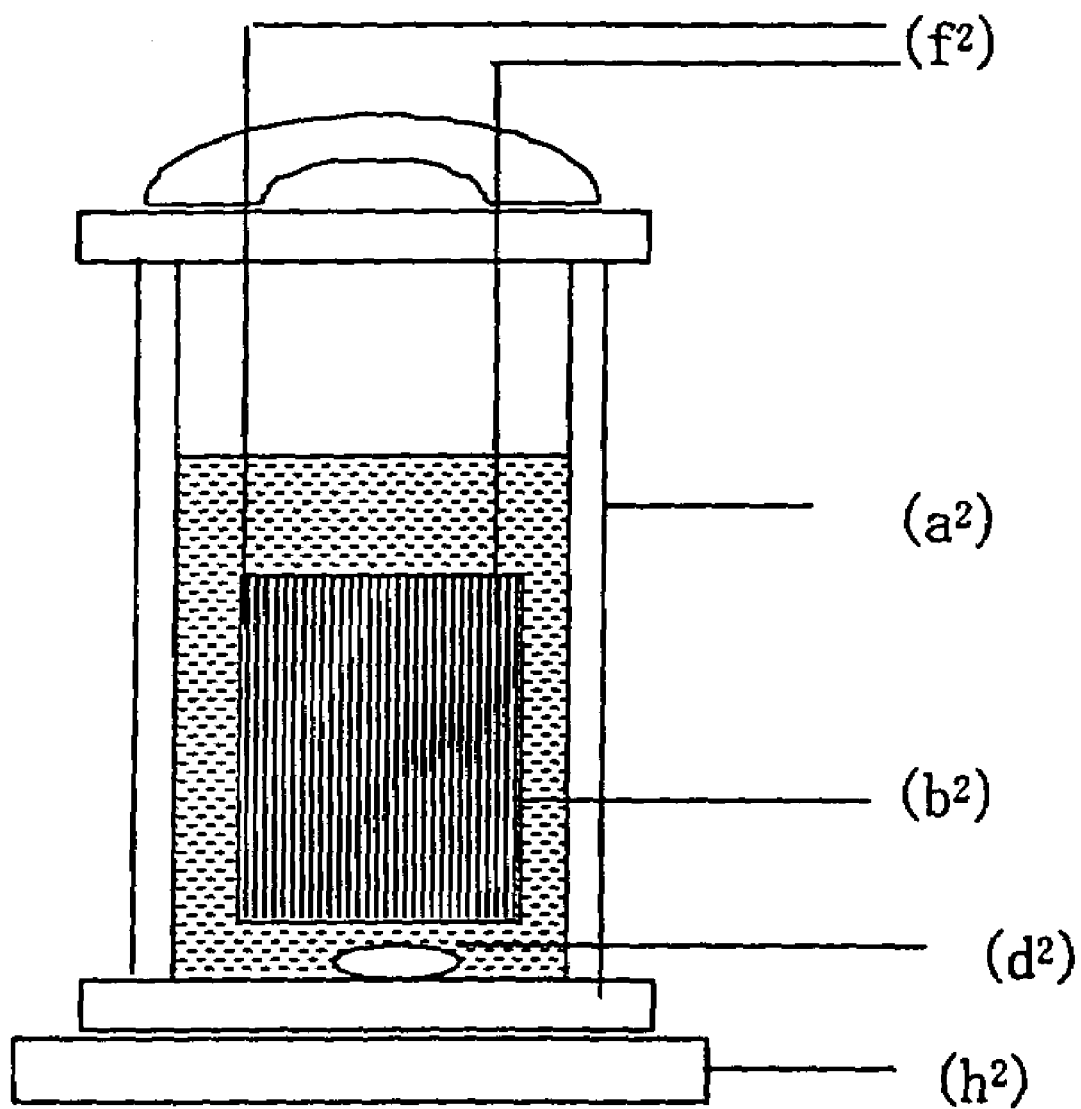
FIG. 2 is a schematic diagram of an immersing type of apparatus for producing microspheres.

For preparing microspheres by using an apparatus as shown in FIG. 2, the emulsion to be subjected to an in-water drying is filled in a closed vessel ($a^2$), and a cylindrical hollow fiber membrane module ($b^2$) is immersed in the emulsion. In this situation, air is passed via a ventilation pathway ($f^2$) with stirring the emulsion by a magnetic stirrer ($h^2$) and a magnetic stirring piece ($d^2$), whereby the organic solvent in the emulsion is passed and permeated through the hollow fiber membrane and is efficiently evaporated off to out of the system, and thereby the microspheres are formed in the closed vessel ($a^2$).

Figure 3:
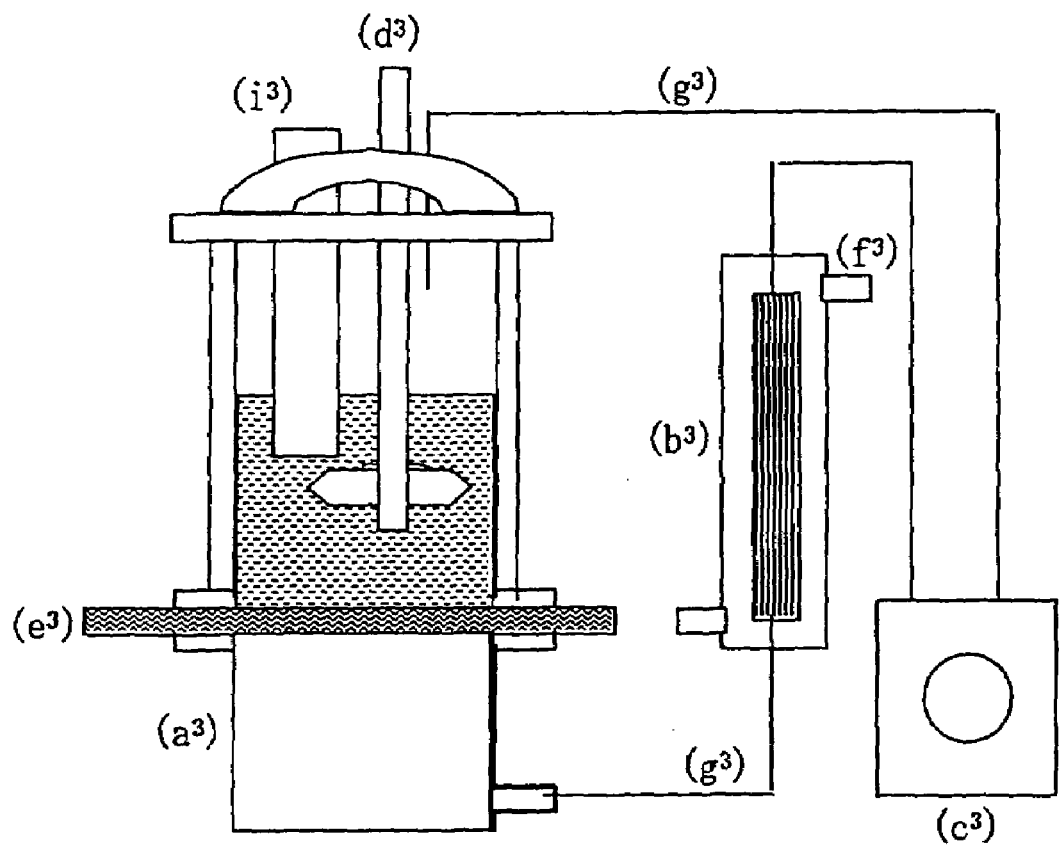
FIG. 3 is a schematic diagram of a circular type of apparatus for producing microspheres provided with emulsifying function.

For preparing microspheres by using an apparatus as shown in FIG. 3, the oil phase and aqueous phase of the emulsion to be subjected to an in-water drying are filled in a closed vessel ($a^3$) and emulsified with a homogenizer ($i^3$). After emulsifying, a portion of the aqueous phase of the emulsion passed through a filter ($e^3$) (e.g., a stainless mesh) provided at the middle of the closed vessel ($a^3$) is circulated with stirring with a stirring blade ($d^3$) by passing through a hollow fiber membrane module by the use of a circulation pump ($c^3$) via a circulation pathway ($g^3$) made of a silicone rubber, etc. During the circulation, when the portion of the aqueous phase is passed through the hollow fiber membrane module, the organic solvent contained therein is passed and permeated through the hollow fiber membrane and is evaporated through the ventilation (or suction) hole ($f^3$) and thereby the organic solvent can be efficiently evaporated off to out of the system, and thereby the microspheres are formed above the filter ($e^3$) provided in the closed vessel ($a^3$).

Figure 4:
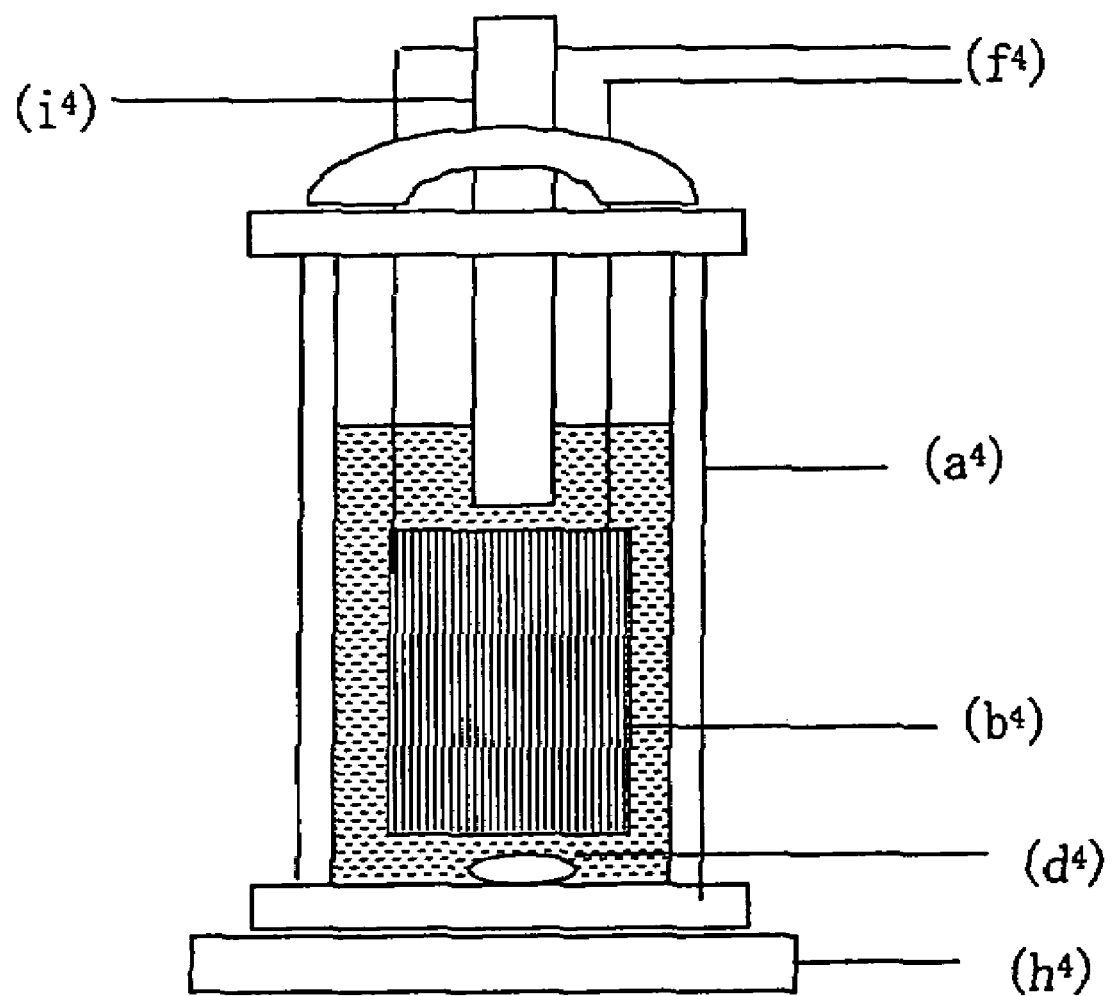
FIG. 4 is a schematic diagram of an immersing type of apparatus for producing microspheres provided with emulsifying function.

For preparing microspheres by using an apparatus as shown in FIG. 4, the oil phase and aqueous phase of the emulsion to be subjected to an in-water drying are filled in a closed vessel ($a^4$) and emulsified with a homogenizer ($i^4$). After emulsifying, a cylindrical hollow fiber membrane module ($b^4$) is immersed in the emulsion. In this situation, air is passed via a ventilation pathway ($f^4$) with stirring the emulsion by a magnetic stirrer ($h^4$) and a magnetic stirring piece ($d^4$), whereby the organic solvent in the emulsion is passed and permeated the hollow fiber membrane and is efficiently evaporated off to out of the system, and thereby the microspheres are formed in the closed vessel ($a^4$).

Figure 5:
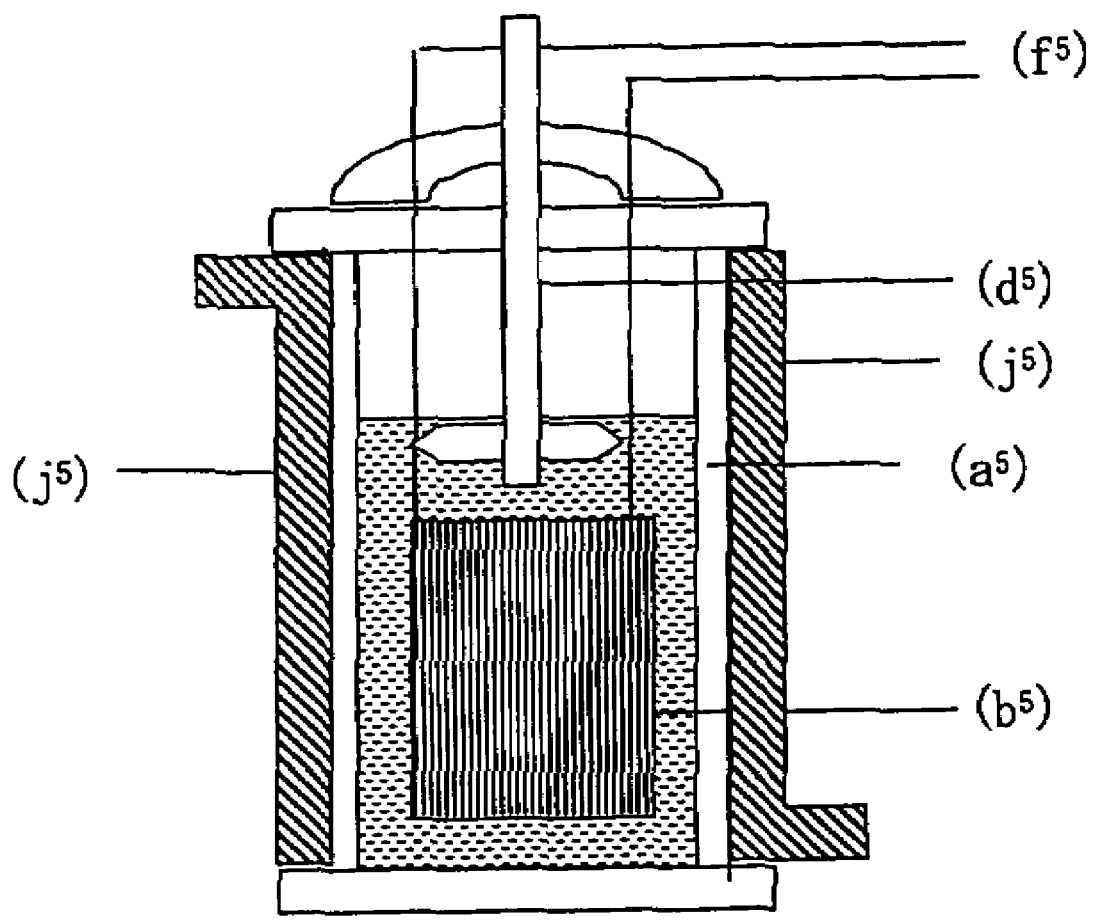
FIG. 5 is a schematic diagram of an immersing type of apparatus for producing microspheres with a function of controlling temperature.

For preparing microspheres by using an apparatus as shown in FIG. 5, the emulsion to be subjected to an in-water drying is filled in a closed vessel ($a^5$) and a cylindrical hollow fiber membrane module ($b^5$) is immersed in the emulsion. In this situation, air is passed via a ventilation pathway ($f^5$) with stirring the emulsion by a stirring blade ($d^5$), whereby the organic solvent in the emulsion is passed and permeated the hollow fiber membrane and is efficiently evaporated off to out of the system, and thereby the microspheres are formed in the closed vessel ($a^5$). In this apparatus, the temperature of the emulsion can be controlled by a temperature controlling jacket ($j^5$), and hence, the organic solvent can more effectively be evaporated off to out of the system.

In the apparatuses of FIG. 1 to FIG. 5, the ventilation (suction) hole ($f^1$), ($f^3$) and the ventilation pathway ($f^2$), ($f^4$), ($f^5$) may optionally be connected to an apparatus for recovering the organic solvent which has functions of cooling, adsorbing, etc.

Example 1

(1) To a lactic acid-glycolic acid copolymer (average molecular weight: 10,000; lactic acid:glycolic acid=1:1; PLGA 5010, manufactured by Wako Pure Chemical Industries, Ltd.) (0.45 g) is added methylene chloride (specific grade reagent, manufactured by Katayama Chemical Industries, Ltd.) (0.75 g), and the mixture is mixed well with a mixer (Touch Mixer MT-51, manufactured by Yamato) to give a homogeneous solution, which is used as an oil phase.

The oil phase is added to a 0.5% aqueous solution of polyvinyl alcohol (Poval 220C, manufactured by Kuraray Co., Ltd.) (3 mL), and the mixture is emulsified with a homogenizer (POLYTRON Homomixer; Kinematica AG, Littau, the diameter of tip: 7 mm) at 2,500 rpm for 5 minutes to give an O/W type emulsion.

(2) The emulsion is poured into a cylindrical closed vessel (inner diameter: 80 mm, inner volume: 800 mL) of the apparatus as shown in FIG. 1 wherein 500 mL of water is previously added, and it is stirred with four stirring blades (diameter: 50 mm, propeller R type, manufactured by HEIDON) which are provided onto a three-one motor (BL-600, manufactured by HEIDON) at 400 rpm at room temperature for one hour.

Thereafter, simultaneously with stirring with four stirring blades, the aqueous phase passed through a stainless mesh filter (opening size: 20 μm) provided at a lower part of the vessel is introduced into a silicone rubber hollow fiber membrane module, whereby methylene chloride is evaporated off under reduced pressure (outer pressure: 80 kPa) to the outside of the hollow fiber membrane, and the aqueous phase passed through the silicone rubber hollow fiber membrane module is returned to the vessel. The circulation is continued at a rate of 250 mL/minute for 2 hours.

The used silicone rubber hollow fiber membrane module is NAGASEP M40-A (manufactured by Nagayanagi Kogyo Kabushiki Kaisha) of the following specifications:

| | |
|---|---|
| Thickness of the hollow fiber membrane: | 40 μm |
| Inner diameter of the hollow fiber membrane: | 170 μm |
| Number of hollow fibers: | 3000 |
| Effective area of the hollow fiber membranes: | 0.3 m$^2$ |

(3) The contents of the closed vessel are passed through a mesh defined by Japanese Pharmacopeia (100 mesh, opening size: 150 μm) and thereafter the microsphere particles are separated with a stainless mesh filter (opening size: 20 μm). The microsphere particles thus obtained are washed with distilled water several times and then transferred to a glass-made sample tube (the full volume: 5 mL, manufactured by Iuchi Seieido) and thereto is added a small amount of distilled water, and the mixture is lyophilized with a lyophilizer (RLE-52ES, manufactured by Kyowa Shinku Co.) at −20° C. for 3 hours (outer pressure: not more than 0.3 kPa) and at 20° C. (outer pressure: not more than 0.3 kPa) for 15 hours to give microsphere particles (average particle size: 60 μm).

The microsphere powder thus obtained (0.01 g) is dissolved in chloroform (for high performance liquid chromatography, manufactured by Kanto Kagaku K.K.) (10 mL) to give a test sample liquid. The test sample liquid (2 μL) is measured with a gas chromatogram apparatus (the main body GC-14B, Integrator CR-7A, manufactured by Shimadzu Corporation) [column packing; Gaschropack 54 (manufactured by GL Science), column temperature: 150° C.; the detector: FID; injection temperature: 170° C.; mobile gas: nitrogen gas; flow rate: 60 mL/h], and based on a calibration curve previously prepared with a standard solution of methylene chloride in chloroform, the concentration of the test sample liquid is estimated, and then in the light of the weight of microsphere particles to be used, the content of the methylene chloride in the microsphere particles are calculated. As a result, it was 25,000 ppm.

Example 2

In the same manner as described in Example 1 except that the stirring period of time is for 30 minutes and the circulation period of time in the silicone rubber hollow fiber membrane module is for one hour, microsphere particles having an average particle size of 69 μm are produced.

Besides, the content of methylene chloride in the microsphere particles was calculated in the same manner as described in Example 1-(3). As a result, it was 30,000 ppm.

Example 3

(1) The O/W type emulsion obtained in Example 1-(1) is poured into a cylindrical closed vessel (inner diameter: 80 mm, inner volume: 800 mL) of the apparatus shown in FIG. 1 wherein 500 mL of water is previously added, and it is stirred with four stirring blades (diameter: 50 mm, propeller R type, manufactured by HEIDON) which are provided onto a three-one motor (BL-600, manufactured by HEIDON) at 400 rpm at room temperature, and simultaneously, the aqueous phase passed through a stainless mesh filter (opening size: 20 μm) provided at a lower part of the vessel is introduced into a silicone rubber hollow fiber membrane module, whereby methylene chloride is evaporated off under reduced pressure (outer pressure: 80 kPa) to the outside of the hollow fiber membrane, and the aqueous phase passed through the silicone rubber hollow fiber membrane module is returned to the vessel. The circulation is continued at a rate of 250 mL/minute for one hour.

The used silicone rubber hollow fiber membrane module is the same as used in Example 1-(2).

(2) In the same manner as described in Example 1-(3), the contents of the closed vessel are treated to give microsphere particles having an average particle size of 66 μm.

Besides, the content of methylene chloride in the microsphere particles was calculated in the same manner as described in Example 1-(3). As a result, it was 32,000 ppm.

Example 4

(1) The O/W type emulsion obtained in Example 1-(1) is poured into a cylindrical closed vessel (inner diameter: 80 mm, inner volume: 800 mL) of the apparatus shown in FIG. 1 wherein 500 mL of water is previously added, and it is stirred with four stirring blades (diameter: 5 cm, propeller R type, manufactured by HEIDON) which are provided onto a three-one motor (BL-600, manufactured by HEIDON) at 200 rpm at room temperature, and simultaneously, the aqueous phase passed through a stainless mesh filter (opening size: 20 μm) provided at a lower part of the vessel is introduced into a silicone rubber hollow fiber membrane module, whereby methylene chloride is evaporated off under reduced pressure (outer pressure: 80 kPa) to the outside of the hollow fiber membrane, and the aqueous phase passed through the silicone rubber hollow fiber membrane module is returned to the vessel. The circulation is continued at a rate of 100 mL/minute for one hour.

The used silicone rubber hollow fiber membrane module is the same one as used in Example 1-(2).

(2) In the same manner as described in Example 1-(3), the contents of the closed vessel are treated to give microsphere particles having an average particle size of 64 μm.

Besides, the content of methylene chloride in the microsphere particles was calculated in the same manner as described in Example 1-(3). As a result, it was 30,000 ppm.

Example 5

(1) To a mixture of fine particles (0.2 g) of vitamin $B_{12}$ (average diameter: 3 μm, manufactured by Rhône-Poulenc) and a lactic acid-glycolic acid copolymer (average molecular weight: 10,000; lactic acid: glycolic acid=1:1; PLGA 5010, manufactured by Wako Pure Chemical Industries, Ltd.) (1.8 g) is added methylene chloride (3 g), and the mixture is mixed well with a bath type sonicator (Sonorex Super RK514BH, manufactured by Banderine) to give a homogeneous dispersion, which is used as an oil phase.

The oil phase is added to a 0.5% aqueous solution of polyvinyl alcohol (Poval 220C, manufactured by Kuraray Co., Ltd.) (8 mL), and the mixture is emulsified with a homogenizer (POLYTRON Homomixer; Kinematica AG, Littau, the diameter of tip: 10 mm) at 2,500 rpm for 5 minutes to give an O/W type emulsion.

(2) The emulsion is poured into a closed vessel (inner diameter: 80 mm, inner volume: 800 mL) of the apparatus shown in FIG. 1 wherein 500 mL of water is previously added, and it is stirred with four stirring blades (diameter: 50 mm, propeller R type, manufactured by HEIDON) which are provided onto a three-one motor (BL-600, manufactured by HEIDON) at 400 rpm at room temperature for 30 minutes.

Thereafter, simultaneously with stirring with four stirring blades, the aqueous phase passed through a stainless mesh filter (opening size: 20 μm) provided at a lower part of the vessel is introduced into a silicone rubber hollow fiber membrane module as described in Example 1, whereby methylene chloride is evaporated off under reduced pressure (outer pressure: 80 kPa) to the outside of the hollow fiber membrane, and the aqueous phase passed through the silicone rubber hollow fiber membrane module is returned to the vessel. The circulation is continued at a rate of 250 mL/minute for one hour.

(3) The contents of the closed vessel are treated in the same manner as described in Example 1-(3), red color microsphere particles (average particle size: 70 μm) are obtained.

The microsphere particles thus obtained (0.01 g) are weighed and thereto is added acetonitrile (5 mL) and the microsphere particles are dissolved. To the solution is added a 0.5 M aqueous sodium chloride solution (10 mL), and the mixture is subjected to centrifugation at 2,000 rpm for 5 minutes to separate the precipitates.

As to the resulting supernatant, an absorbance at 360 nm is measured with a spectrophotometer (UV-2500PC, manufactured by Shimadzu Corporation), and based on a calibration curve previously prepared, the content of vitamin $B_{12}$ was estimated, and then in the light of the weight of microsphere particles, the content of vitamin $B_{12}$ in the microsphere particles was calculated. As a result, it was 7.8%.

Besides, when it was calculated based on the amount of vitamin $B_{12}$ used, the content of vitamin $B_{12}$ in the microsphere particles and the produced amount of microsphere particles, 78% of vitamin $B_{12}$ used was taken into the microsphere particles.

Moreover, the content of methylene chloride in the microsphere particles was calculated in the same manner as described in Example 1-(3). As a result, it was 21,000 ppm.

Example 6

(1) To a mixture of fine particles (0.25 g) of vitamin $B_{12}$ (average diameter: 3 μm, manufactured by Rhône-Poulenc) and a lactic acid-glycolic acid copolymer (average molecular weight: 10,000; lactic acid: glycolic acid=1:1; PLGA 5010, manufactured by Wako Pure Chemical Industries, Ltd.) (9.75 g) is added methylene chloride (specific grade reagent, manufactured by Katayama Chemical Industries, Ltd.) (15 g), and the mixture is mixed well with a bath type sonicator (Sonorex Super RK514BH, manufactured by Banderine) to give a homogeneous dispersion, which is used as an oil phase.

The oil phase is added to a 0.5% aqueous solution of polyvinyl alcohol (Poval 220C, manufactured by Kuraray Co., Ltd.) (40 mL), and the mixture is emulsified with a homogenizer (POLYTRON Homomixer; Kinematica AG, Littau, the diameter of tip: 20 mm) at 2,500 rpm for 5 minutes to give an O/W type emulsion.

(2) The emulsion is poured into a cylindrical closed vessel (inner diameter: 110 mm, inner volume: 1 L) of the apparatus shown in FIG. 2 wherein 500 mL of water is previously added, and it is stirred with a magnet stirrer (IS-3DS, manufactured by Ikeda Rika) and a Tefron-coated stirring piece (40 mm in size) at 600 rpm at room temperature, and simultaneously, methylene chloride is evaporated off from the vessel by using a cylindrical silicone rubber hollow fiber membrane module inserted within the vessel, wherein nitrogen gas is passed through the inside of the hollow fibers. The nitrogen gas is passed at a rate of 4.5 L/minute. This treatment is carried out for one hour.

The used cylindrical silicone rubber hollow fiber membrane module is NAGASEP M60-1800 in a cylindrical shape of the following specifications:

| | |
|---|---|
| Diameter of the cylinder: | 100 mm |
| Dimension of the cylinder: | 120 mm × 120 mm |
| Thickness of the hollow fiber membrane: | 60 μm |
| Inner diameter of the hollow fiber membrane: | 200 μm |
| Outer diameter of the hollow fiber membrane: | 320 μm |
| Number of hollow fibers: | 1800 |
| Effective area of the hollow fiber membranes: | 0.15 m² |

(3) The contents of the closed vessel are treated in the same manner as described in Example 1-(3) to give red color microsphere particles (average particle size: 59.6 μm) (yield: 78%).

By calculating in the same manner as described in Example 1-(3) and Example 5-(3), the content of vitamin $B_{12}$ and the content of methylene chloride in the microsphere particles were 2.3% and 36,000 ppm, respectively, and 90.3% of vitamin $B_{12}$ used was taken into the microsphere particles.

Example 7

(1) To a mixture of fine particles (0.1 g) of vitamin $B_{12}$ (average diameter: 3 μm, manufactured by Rhône-Poulenc) and a lactic acid-glycolic acid copolymer (average molecular weight: 10,000; lactic acid: glycolic acid=1:1; PLGA 5010, manufactured by Wako Pure Chemical Industries, Ltd.) (0.9 g) is added methylene chloride (2 g), and the mixture is mixed well with a bath type sonicator (Sonorex Super RK514BH, manufactured by Banderine) to give a homogeneous dispersion, which is used as an oil phase.

The oil phase is entered into a cylindrical closed vessel (inner diameter: 80 mm, inner volume: 800 mL) as shown in FIG. 3, wherein a 0.5% aqueous solution of polyvinyl alcohol (Gosenol EG-40, manufactured by The Nippon Synthetic Chemical Industry Co., Ltd.) (400 mL) is previously filled, and it is emulsified with a homogenizer (POLY- TRON Homomixer; Kinematica AG, Littau, the diameter of tip: 20 mm) at 8,000 rpm for 3 minutes to give an O/W type emulsion.

(2) The emulsion is stirred with four stirring blades (diameter: 50 mm, propeller R type, manufactured by HEIDON) which are provided onto a three-one motor (BL-600, manufactured by HEIDON) at 400 rpm at room temperature for 30 minutes.

Thereafter, simultaneously with stirring with four stirring blades, the aqueous phase passed through a stainless mesh filter (opening size: 20 μm) provided at a lower part of the vessel is introduced into a silicone rubber hollow fiber membrane module as described in Example 1, whereby methylene chloride is evaporated off under reduced pressure (outer pressure: 80 kPa) to the outside of the hollow fibers, and the aqueous phase passed through the silicone rubber hollow fiber membrane module is returned to the vessel. The circulation is continued at a rate of 250 mL/minute for one hour.

(3) The contents of the closed vessel are transferred into a 50 mL volume Teflon-made centrifuge tube and centrifuged with a centrifugal separator (KN-30F, manufactured by Kubota Shoji K.K.) at 2,000 rpm for 5 minutes, and the supernatant is discharged. The precipitated particles are washed with a small amount of water, and subjected to the centrifugation like the above. This centrifugation is repeated three times, and the finally obtained microsphere particles are lyophilized in the same manner as described in Example 1 to give red color microsphere particles (average particle size: 34.8 μm).

By calculating in the same manner as described in Example 1-(3) and Example 5-(3), the content of vitamin $B_{12}$ and the content of methylene chloride in the microsphere particles were 7.9% and 13,500 ppm, respectively, and 79.0% of vitamin $B_{12}$ used was taken into the microsphere particles.

Example 8

(1) To a mixture of fine particles (0.1 g) of vitamin $B_{12}$ (average diameter: 3 μm, manufactured by Rhône-Poulenc) and a lactic acid-glycolic acid copolymer (average molecular weight: 10,000; lactic acid: glycolic acid=1:1; PLGA 5010, manufactured by Wako Pure Chemical Industries, Ltd.) (0.9 g) is added methylene chloride (2 g), and the mixture is mixed well with a bath type sonicator (Sonorex Super RK514BH, manufactured by Banderine) to give a homogeneous dispersion, which is used as an oil phase.

The oil phase is entered into a cylindrical closed vessel (inner diameter: 110 mm, inner volume: 1 L) as shown in FIG. 4, wherein a 0.5% aqueous solution of polyvinyl alcohol (Gosenol EG-40, manufactured by The Nippon Synthetic Chemical Industry Co., Ltd.) (400 mL) is previously filled, and it is emulsified with a homogenizer (POLYTRON Homomixer; Kinematica AG, Littau, the diameter of tip: 20 mm) at 8,000 rpm for 3 minutes to give an O/W type emulsion.

(2) The emulsion is stirred with a magnet stirrer (IS-3DS, manufactured by Ikeda Rika) and a Tefron-coated stirring piece (40 mm in size) at 600 rpm at room temperature, and simultaneously, methylene chloride is evaporated off from the vessel by using a cylindrical silicone rubber hollow fiber membrane module inserted within the vessel, wherein nitrogen gas is passed through the inside of the hollow fibers. The nitrogen gas is passed at a rate of 2.4 L/minute. This treatment is carried out for one hour.

The used cylindrical silicone rubber hollow fiber membrane module is the same one as used in Example 6.

(3) The resultant is treated in the same manner as described in Example 7-(3) to give red color microsphere particles (average particle size: 29.0 μm).

By calculating in the same manner as described in Example 1-(3) and Example 5-(3), the content of vitamin $B_{12}$ and the content of methylene chloride in the microsphere particles were 7.3% and 12,900 ppm, respectively, and 73.0% of vitamin $B_{12}$ used was taken into the microsphere particles.

Example 9

(1) To a mixture of fine particles (0.1 g) of vitamin $B_2$ (average diameter: 3 μm, manufactured by Rhône-Poulenc) and a lactic acid-glycolic acid copolymer (average molecular weight: 10,000; lactic acid: glycolic acid=1:1; PLGA 5010, manufactured by Wako Pure Chemical Industries, Ltd.) (0.9 g) is added methylene chloride (2 g), and the mixture is mixed well with a bath type sonicator (Sonorex Super RK514BH, manufactured by Banderine) to give a homogeneous dispersion, which is used as an oil phase.

The oil phase is added to a 0.5% aqueous solution of polyvinyl alcohol (Poval 220C, manufactured by Kuraray Co., Ltd.) (4 mL), and it is emulsified with a homogenizer (POLYTRON Homomixer; Kinematica AG, Littau, the diameter of tip: 10 mm) at 2,500 rpm for 5 minutes to give an O/W type emulsion.

(2) The emulsion is poured into a cylindrical closed vessel (inner diameter: 110 mm, inner volume: 1 L) as shown in FIG. 5 wherein 500 mL of water is previously added, and the mixture is stirred with four stirring blades (diameter: 50 mm, propeller R type, manufactured by HEIDON) which are provided onto a three-one motor (BL-600, manufactured by HEIDON) at 400 rpm at room temperature, and simultaneously, methylene chloride is evaporated off from the vessel by using a cylindrical silicone rubber hollow fiber membrane module inserted within the vessel, wherein nitrogen gas is passed through the inside of the hollow fibers for one hour. The nitrogen gas is passed at a rate of 3.6 L/minute. Subsequently, with continuing the passing of nitrogen gas under the same conditions, water having a temperature of 40° C. is circulated into the jacket outside of the closed vessel with an apparatus for circulating water having a constant temperature (RM-6, manufactured by Rauda) to heat the emulsion for 3 hours. Moreover, with continuing the passing of nitrogen gas under the same conditions, the temperature of the circulating water is raised to 60° C. and the procedure for removal of methylene chloride is continued for one hour. After completion of the procedure, with continuing the passing of nitrogen gas under the same conditions, the temperature of the circulating water is lowered to about 5° C., and the emulsion is cooled until about 30° C. or lower.

The used cylindrical silicone rubber hollow fiber membrane module is the same as used in Example 6.

(3) The resultant is treated in the same manner as described in Example 1-(3) to give red color microsphere particles (average particle size: 57.8 μm).

By calculating in the same manner as described in Example 1-(3) and Example 5-(3), the content of vitamin $B_{12}$ and the content of methylene chloride in the microsphere particles were 4.3% and less than 200 ppm, respectively, and 42.9% of vitamin $B_{12}$ used was taken into the microsphere particles.

Example 10

(1) A lactic acid-glycolic acid copolymer (average molecular weight: 8,000; lactic acid:glycolic acid=1:1; RG502H; manufactured by Boehringer Ingelheim) (0.45 g) and taltirelin hydrate (TRH derivative) (50 mg) are weighed and put into a glass-made test tube, and thereto is added a mixture of methylene chloride (specific grade reagent, manufactured by Katayama Chemical Industries, Ltd.) (2 mL) and ethanol (specific grade reagent, manufactured by Katayama Chemical Industries, Ltd.) (0.5 mL), and the mixture is mixed well with a mixer (Touch Mixer MT-51, manufactured by Yamato) to give a homogeneous solution.

This solution is evaporated to dryness by using a block heater (Dry Block Bath MG-2, manufactured by Tokyo Rikakikai Co., Ltd.) heated at about 60° C. for about 30 minutes under nitrogen current. Then, the organic solvent therein is further evaporated off by using a scaled-down lyophilizer (Speed Back Concentrator, manufactured by SABATO) to give a solid solution.

(2) To the resulting solid solution is added methylene chloride (1 g), and the mixture is mixed well by using a mixer (Touch Mixer MT-51, manufactured by Yamato) to give a homogeneous solution, which is used as an oil phase.

(3) The oil phase is entered into a cylindrical closed vessel (inner diameter: 100 mm, inner volume: 1,000 mL) as shown in FIG. 5, wherein a 0.5% aqueous solution of polyvinyl alcohol (Gosenol EG-40, manufactured by The Nippon Synthetic Chemical Industry Co., Ltd.) (400 mL) is previously filled and to which a plate-type silicone rubber hollow fiber membrane module is provided, and it is emulsified with a homogenizer (POLYTRON Homomixer; Kinematica AG, Littau, the diameter of tip: 20 mm) at 20,000 rpm for 3 minutes to give an O/W type emulsion. The plate-type silicone rubber hollow fiber membrane module used is NAGASEP M60-290L-650 of the following specifications, and during the emulsification procedure, the nitrogen gas is passed through the inside of the hollow fiber membrane at a rate of 1.2 L/minute.

| | |
|---|---|
| Effective length of the hollow fiber membrane: | 290 mm |
| Thickness of the hollow fiber membrane: | 60 μm |
| Inner diameter of the hollow fiber membrane: | 200 μm |
| Outer diameter of the hollow fiber membrane: | 320 μm |
| Number of hollow fibers: | 650 |
| Effective area of the hollow fiber membranes: | 0.15 m² |

(4) After the emulsification, the tip for emulsification is quickly taken out while the passing of the nitrogen gas is continued, and it is stirred with four stirring blades (diameter: 50 mm, propeller R type, manufactured by HEIDON) which are provided onto a three-one motor (BL-600, manufactured by HEIDON) at 400 rpm at room temperature for one hour, by which the methylene chloride is removed from the vessel.

(5) After completion of the above procedure, the contents of the closed vessel (dispersion of microspheres) are passed through a stainless mesh filter (opening size: 20 μm), and transferred into a 50 mL volume Teflon-made centrifuge tube, which is centrifuged with a centrifugal separator (KN-30F, manufactured by Kubota Shoji K.K.) at 2,000 rpm for 10 minutes, and the supernatant is discharged. The precipitated particles are washed with a small amount of water, and subjected to the centrifugation like the above. This centrifugation is repeated three times, and the finally obtained microsphere particles are transferred to a glass-made sample tube (the full volume: 5 mL, manufactured by Iuchi Seieido) and thereto is added a small amount of distilled water, and the mixture is lyophilized with a lyophilizer (RLE-52ES, manufactured by Kyowa Shinku Co.) at 20° C. (outer pressure: not more than 0.3 kPa) for 15 hours to give white color microsphere particles (average particle size: 7 μm).

(6) The microsphere particles thus obtained (0.01 g) were weighed and dissolved in acetonitrile (3 mL), and thereto was added a 0.035 M formate buffer (pH 3.0, 2 mL), and the mixture was centrifuged at 2,000 rpm for 5 minutes. The supernatant (200 μL) was measured by HPCL method, and based on a calibration curve previously prepared, the content of the medicament is estimated, and then in the light of the weight of microsphere particles used, the content of the medicament in the microsphere particles is calculated. As a result, it was 8.9%. Besides, when it was calculated based on the amount of the medicament used, the content of the medicament in the microsphere particles and the produced amount of microsphere particles, 89% of the medicament used was taken into the microsphere particles.

(7) The microsphere particles thus obtained (0.02 g) were dissolved in chloroform (for high performance liquid chromatography, manufactured by Kanto Kagaku K.K.) (1 mL) to give a test sample liquid. The test sample liquid (2 μL) was measured with a gas chromatogram apparatus (the main body GC-14B, Integrator CR-7A, manufactured by Shimadzu Corporation) [column packing; Gaschropack 54 (manufactured by GL Science), column temperature: 150° C.; the detector: FID; injection temperature: 170° C.; mobile gas: nitrogen gas; flow rate: 60 mL/h], and based on a calibration curve previously prepared with a standard solution of methylene chloride in chloroform, the concentration of the test sample liquid was estimated, and then in the light of the weight of microsphere particles used, the content of the methylene chloride in the microsphere particles was calculated. As a result, it was below detection limits (i.e., below 100 ppm).

Example 11

To a solid solution prepared in the same manner as described in Example 10-(1) (double amount of Example 10-(1)) is added methylene chloride (2 g), and the mixture is mixed well by using a mixer (Touch Mixer MT-51, manufactured by Yamato) to give a homogeneous solution, which is used as an oil phase. The oil phase is treated in the same manner as described in Example 10-(3) to -(5) except that the amount of a 0.5% aqueous solution of polyvinyl alcohol is the same as that in Example 10-(3) to give white color microsphere particles (average particle size: 7 μm).

By calculating in the same manner as described in Example 10-(6) and -(7), the content of the medicament and the content of methylene chloride in the microsphere particles were 10% and 130 ppm, respectively, and 100% of the medicament used was taken into the microsphere particles.

Example 12

To a solid solution prepared in the same manner as described in Example 10-(1) (4-fold amount of Example 10-(1)) is added methylene chloride (4 g), and the mixture is mixed well by using a mixer (Touch Mixer MT-51, manufactured by Yamato) to give a homogeneous solution, which is used as an oil phase. The oil phase is treated in the same manner as described in Example 10-(3) to -(5) except that the amount of a 0.5% aqueous solution of polyvinyl alcohol is the same as that in Example 10-(3) to give white color microsphere particles (average particle size: 7 μm).

By calculating in the same manner as described in Example 10-(6) and -(7), the content of the medicament and the content of methylene chloride in the microsphere particles were 10% and 270 ppm, respectively, and 100% of the medicament used was taken into the microsphere particles.

Example 13

A polylactic acid (average molecular weight: 20,000; R202H; manufactured by Boehringer Ingelheim) (0.225 g) and leuprorelin acetate (LHRH derivative, manufactured by BACHEM AG) (25 mg) are weighed and put into a glass-made test tube, and thereto is added a mixture of methylene chloride (specific grade reagent, manufactured by Katayama Chemical Industries, Ltd.) (1.3 mL) and ethanol (specific grade reagent, manufactured by Katayama Chemical Industries, Ltd.) (0.25 mL), and the mixture is mixed well with a mixer (Touch Mixer MT-51, manufactured by Yamato) to give a homogeneous solution.

This solution is evaporated to dryness by using a block heater (Dry Block Bath MG-2, manufactured by Tokyo Rikakikai Co., Ltd.) heated at about 60° C. for about 30 minutes under nitrogen current. Then, the organic solvent therein is evaporated off by using a scaled-down lyophilizer (Speed Back Concentrator, manufactured by SABATO) to give a solid solution.

The resulting solid solution is treated in the same manner as described in Example 10-(2) to -(5) except that the amounts of methylene chloride and a 0.5% aqueous solution of polyvinyl alcohol are the same as those in Example 10. After completion of the above procedure, the contents of the closed vessel (dispersion of microspheres) are passed through a polyvinylidene difluoride membrane filter (membrane diameter: 25 mm, membrane pore size: 5 μm, Durapore SVLP025, manufactured by Nihon Millipore Corporation) to separate microsphere particles. The resulting microsphere particles are transferred to a glass-made sample tube (the full volume: 5 mL, manufactured by Iuchi Seieido) and thereto is added a small amount of distilled water, and the mixture is lyophilized with a lyophilizer (RLE-52ES, manufactured by Kyowa Shinku Co.) at 20° C. (outer pressure: not more than 0.3 kPa) for 15 hours to give white color microsphere particles (average particle size: 12.9 μm).

The microsphere particles thus obtained (5 mg) are weighed and thereto is added acetonitrile (1.5 mL) and the microsphere particles are dissolved. To the solution is added a 0.5 M aqueous sodium chloride solution (3.5 mL), and the mixture is subjected to centrifugation at 2,000 rpm for 10 minutes to separate the precipitates.

The resulting supernatant (200 μL) was measured by HPLC method, and based on a calibration curve previously prepared, the content of leuprorelin acetate (LHRH derivative) was estimated, and then in the light of the weight of microsphere particles, the content of leuprorelin acetate in the microsphere particles was calculated. As a result, it was 7.5%.

Besides, when it was calculated based on the amount of leuprorelin acetate used, the content of leuprorelin acetate in the microsphere particles and the produced amount of microsphere particles, 84.5% of leuprorelin acetate used was taken into the microsphere particles.

Besides, the content of methylene chloride in the microsphere particles was calculated in the same manner as described in Example 10-(7). As a result, it was 520 ppm.

Comparative Example 1

(1) The emulsion obtained in Example 1-(1) is poured into a closed vessel (inner diameter: 80 mm, inner volume: 800 mL) as shown in FIG. 1 wherein 500 mL of water is previously added, and it is stirred with four stirring blades (diameter: 50 mm, propeller R type, manufactured by HEIDON) which are provided onto a three-one motor (BL-600, manufactured by HEIDON) at 400 rpm at room temperature for 3 hours.

(2) The contents of the closed vessel are treated in the same manner as described in Example 1-(3) to give microsphere particles having an average particle size of 80 μm.

Besides, the content of methylene chloride in the microsphere particles was calculated in the same manner as described in Example 1-(3). As a result, it was 31,000 ppm.

Comparative Example 2

(1) The emulsion obtained in Example 1-(1) is poured into a closed vessel (inner diameter: 80 mm, inner volume: 800 mL) as shown in FIG. 1 wherein 500 mL of water is previously added, and it is stirred with four stirring blades (diameter: 50 mm, propeller R type, manufactured by HEIDON) which are provided onto a three-one motor (BL-600, manufactured by HEIDON) at 400 rpm at room temperature for 2 hours.

(2) The contents of the closed vessel are treated in the same manner as described in Example 1-(3) to give microsphere particles having an average particle size of 73 μm.

Besides, the content of methylene chloride in the microsphere particles was calculated in the same manner as described in Example 1-(3). As a result, it was 39,000 ppm.

Comparative Example 3

(1) The emulsion obtained in Example 1-(1) is poured into a closed vessel (inner diameter: 80 mm, inner volume: 800 mL) as shown in FIG. 1 wherein 500 mL of water is previously added, and it is stirred with four stirring blades (diameter: 50 mm, propeller R type, manufactured by HEIDON) which are provided onto a three-one motor (BL-600, manufactured by HEIDON) at 400 rpm at room temperature for one hour.

(2) The contents of the closed vessel are treated in the same manner as described in Example 1-(3) to give microsphere particles having an average particle size of 77 μm.

Besides, the content of methylene chloride in the microsphere particles was calculated in the same manner as described in Example 1-(3). As a result, it was 50,000 ppm.

Comparative Example 4

(1) The emulsion obtained in Example 6-(1) is poured into a closed vessel (inner diameter: 110 mm, inner volume: 1 L) as shown in FIG. 2 wherein 500 mL of water is previously added, and it is stirred with a magnet stirrer (IS-3DS, manufactured by Ikeda Rika) and a Teflon-made stirring piece (40 mm in size) at 600 rpm at room temperature for one hour.

(2) The contents of the closed vessel were treated in the same manner as described in Example 1-(3), but microsphere particles could not be obtained since the content was not solidified.

Comparative Example 5

(1) The emulsion obtained in Example 7-(1) is stirred with four stirring blades (diameter: 50 mm, propeller R type, manufactured by HEIDON) which are provided onto a three-one motor (BL-600, manufactured by HEIDON) in a closed vessel (inner diameter: 80 mm, inner volume: 800 mL) as shown in FIG. 3 at 400 rpm at room temperature for 1.5 hour.

(2) The contents of the closed vessel are treated in the same manner as described in Example 7-(3) to give microsphere particles having an average particle size of 35.4 μm.

Besides, by calculating in the same manner as described in Example 1-(3) and Example 5-(3), the content of vitamin $B_{12}$ and the content of methylene chloride in the microsphere particles were 7.9% and 22,600 ppm, respectively, and 79.2% of vitamin $B_{12}$ used was taken into the microsphere particles.

Experiment 1

Into a closed vessel (inner diameter: 110 mm, inner volume: 1 L) as shown in FIG. 2, a 1% aqueous methylene chloride solution (1 L) was added, and it was stirred with a magnet stirrer (IS-3DS, manufactured by Ikeda Rika) and a Teflon-made stirring piece (40 mm in size) at 600 rpm at room temperature, and simultaneously, methylene chloride was evaporated off from the vessel by using a cylindrical silicone rubber hollow fiber membrane module (NAGASEP M60-1800, cylindrical shape) inserted within the vessel, wherein nitrogen gas was passed through the inside of the hollow fiber membrane. The nitrogen gas was passed at a rate of 130 mL, 520 mL, 1.8 L, and 4 L/minute.

Figure 6:
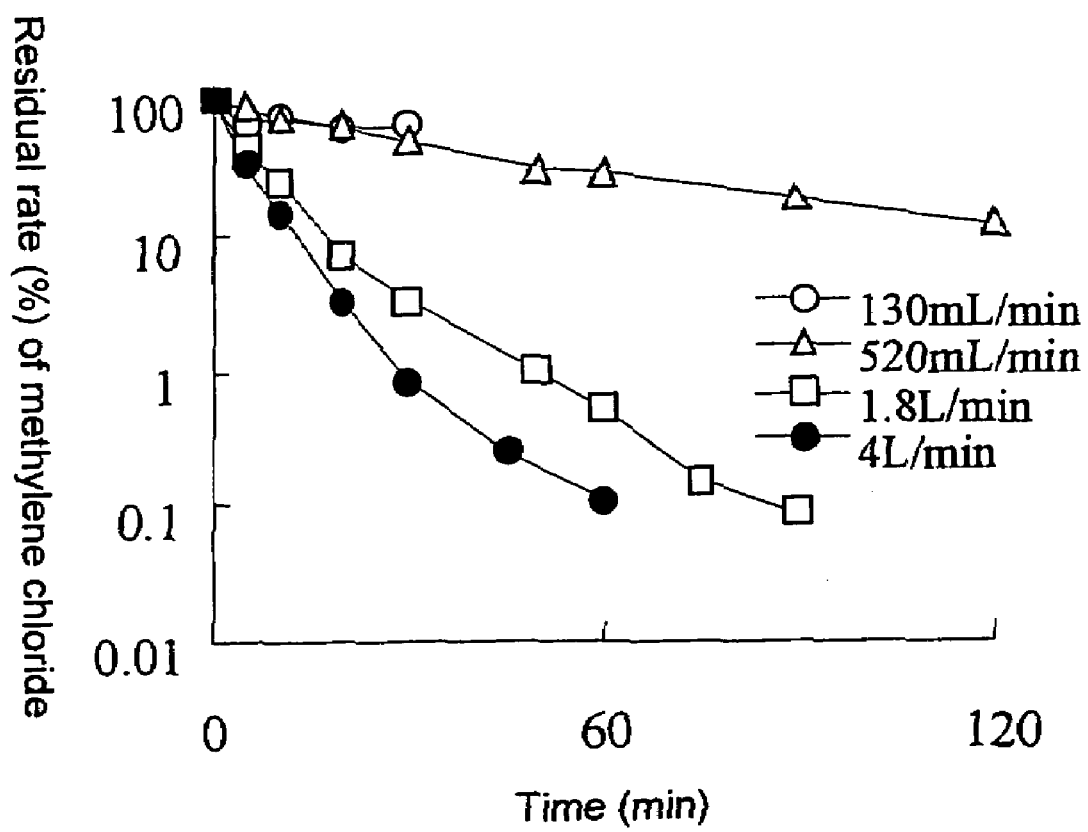
FIG. 6 is a graph showing the correlation between the passing rate of nitrogen gas and the rate of removal of methylene chloride in an immersing type of apparatus for producing microspheres.

With the lapse of constant time, a small amount of the test sample liquid was taken at each time, and the concentration of methylene chloride in the sample liquid was measured with a gas chromatogram apparatus (measured in the same manner as described in Example 1, provided that the concentration of methylene chloride in the sample liquid was calculated with a calibration curve prepared with an aqueous methylene chloride solution). Based on the change of the concentration thereof, the percentage of the concentration of methylene chloride at the time of sampling to the concentration of methylene chloride before the passing of a gas (1% of the aqueous solution being calculated as 100), and the data in correlation with the time were plotted. The graph thus obtained is shown in FIG. 6.

Experiment 2

Figure 7:
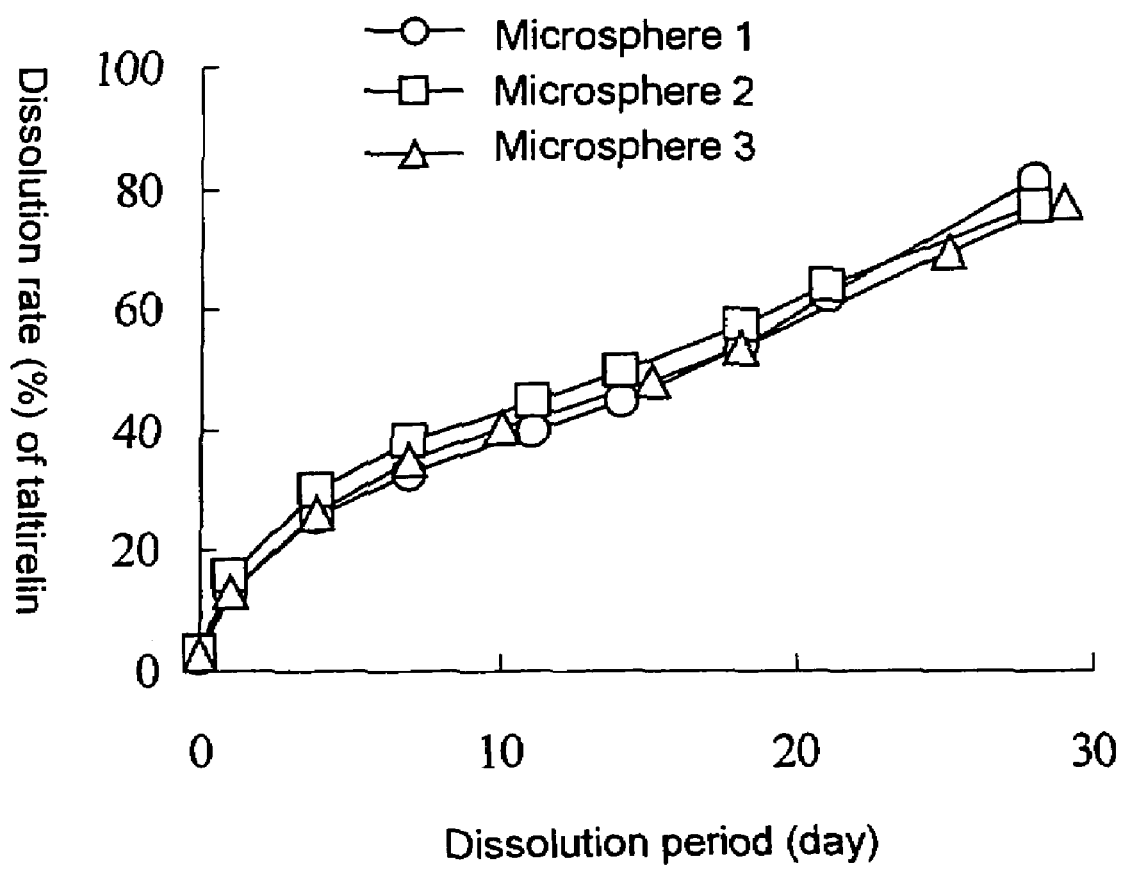
FIG. 7 is a graph showing the change with time of the accumulated amount of taltirelin dissolving out from the microspheres at 37° C.

The taltirelin-containing microsphere preparations obtained in Example 10, 11 and 12 were considered as Microsphere 1, 2, 3, respectively, and 10 mg of each Microsphere was precisely weighed and transferred to a test tube with a cap (volume: 15 mL). To the tube was added a 1/30 M phosphate buffer (pH 7.4, 10 mL), and sealed. The tube was put onto a rotating cultivator (RT-50, manufactured by TAITEC) in an air thermostatic chamber (Biochamber BC-1200, manufactured by TAITEC) controlled at 37° C., and shaken at a rotational speed of 25 rpm. With the lapse of prescribed time, the eluate was taken, and then, additional 1/30 M phosphate buffer of the same volume of the eluate taken was added, and further the same procedures were repeated. The amount of taltirelin dissolving out from microspheres were calculated by HPLC method. The accumulated amount of taltirelin (TRH derivative) dissolving out from microspheres at 37° C. was plotted in correlation with the dissolution period. The graph thus obtained is shown in FIG. 7.

Experiment 3

Figure 8:
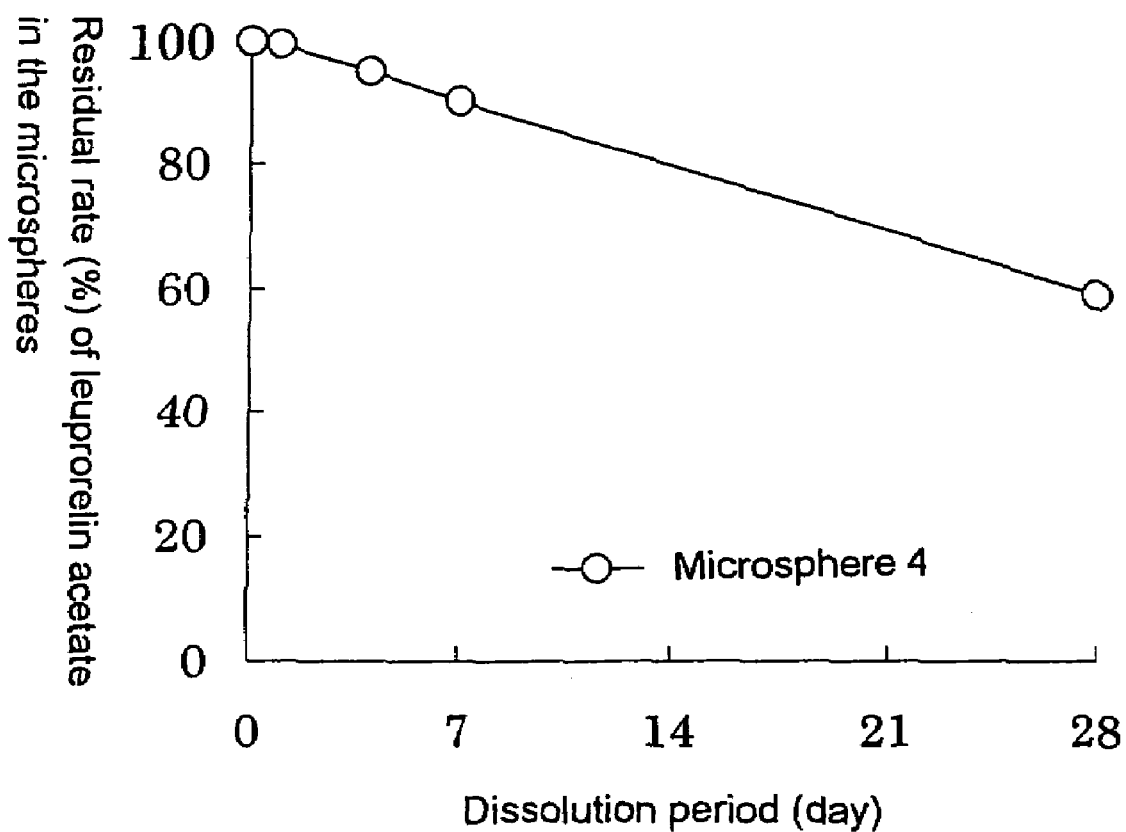
FIG. 8 is a graph showing the change with time in the amount of leuprorelin acetate remained in the microspheres at 37° C.

The leuprorelin acetate-containing microsphere preparation prepared in Example 13 was considered as Microsphere 4, and 5 mg thereof was precisely weighed and transferred to test tubes with a cover (volume: 15 mL). To five test tubes with a cover thus prepared was added a 1/30 M phosphate buffer (pH 7.0, 10 mL) containing 0.05% Tween 80 (polyoxyethylene sorbitan fatty acid ester, manufactured by Nikko Chemicals Co., Ltd.). Each test tube was sealed, and put onto a rotating cultivator (RT-50, manufactured by TAITEC) in an air thermostatic chamber (Biochamber BC-1200, manufactured by TAITEC) controlled at 37° C., and shaken at a rotational speed of 25 rpm. With the lapse of prescribed time, each one tube was taken out, and centrifuged with a centrifugal separator (KN-30F, manufactured by Kubota Shoji K.K.) at 2,000 rpm for 10 minutes in order to precipitate microspheres. The supernatant was discharged, and in order to distill moisture off, the tube was kept in a glass-made desiccator containing silica gel under reduced pressure overnight. To the tube was added acetonitrile (1.5 mL) and the dried microsphere particles were dissolved. Then, a 0.5 M aqueous sodium chloride solution (3.5 mL) was added to the tube, and the tube was centrifuged at 2,000 rpm for 10 minutes to remove the precipitates. The resulting supernatant (200 μL) was measured by HPCL method, and based on a calibration curve previously prepared, the content of leuprorelin acetate remained in the microspheres was estimated. The amount of leuprorelin acetate remained in the microspheres at 37° C. was plotted in correlation with the dissolution period. The graph thus obtained is shown in FIG. 8.

INDUSTRIAL AVAILABLILITY

According to the method of the present invention, when micro-spheres are prepared from an emulsion by an in-water drying method with a gas separation membrane, by supplying an emulsion from one side of the membrane and the organic solvent is evaporated off into the other side thereof, the organic solvent can be removed extremely efficiently, and further the procedures can be done in a closed system, and hence, the improved process of the present invention is extremely excellent also from the environmental viewpoint.

The invention claimed is:

1. An apparatus for the preparation of microspheres by an in-water drying method from an emulsion wherein an organic phase containing an organic solvent having a boiling point lower than that of water and a hardly-water-soluble polymer is emulsified in an aqueous phase, said apparatus comprising:

(a) a vessel for holding the emulsion which vessel is equipped with a filter to take out an aqueous portion of the aqueous phase of the emulsion;

(b) a gas separation membrane module for evaporating off the organic solvent from the aqueous portion;

(c) a circulation pathway which connects the vessel and the gas separation membrane module; and (d) a pump for circulating the aqueous portion through the gas separation membrane module.

2. An apparatus for the preparation of microspheres by an in-water drying method from an emulsion wherein an organic phase containing an organic solvent having a boiling point lower than that of water and a hardly-water-soluble polymer is emulsified in an aqueous phase, said apparatus comprising:

(a) a vessel for holding the emulsion; and (b) a gas separation membrane module for evaporating off the organic solvent from the emulsion, which gas separation membrane module is located within and immersed in the emulsion in the vessel.

3. The apparatus according to claim 1 or claim 2, wherein the gas separation membrane module is a pervaporation membrane module.

4. The apparatus according to claim 3 wherein the gas separation membrane module is a silicon-rubber pervaporation membrane module.

5. The apparatus according to claim 1 or claim 2, wherein the gas separation membrane module is in the form of a bundle of plural gas separation membranes which form hollow fibers.

6. The apparatus according to claim 1, wherein the apparatus further includes one or more of a) means for passing a gas on an other side of the gas separation membrane than the aqueous portion, b) means for decompressing said other side of the gas separation membrane and c) means for warming the emulsion.

7. The apparatus according to claim 2, wherein the apparatus further includes one or more of a) means for passing a gas on an other side of the gas separation membrane than the emulsion and b) means for warming the emulsion.

8. The apparatus according to claim 1, wherein the gas separation membrane module is in the form of a bundle of plural gas separation membranes which form hollow fibers, and is orientated so that the aqueous portion is introduced into an inner side of said gas separation membranes which form hollow fibers and the organic solvent is evaporated to an outside of said gas separation membranes.

9. The apparatus according to claim 2, wherein the gas separation membrane module is in the form of a bundle of plural gas separation membranes which form hollow fibers, and is orientated so that a gas is passed on an inner side of said gas separation membranes which form hollow fibers to evaporate off the organic solvent.

10. The apparatus according to claim 1 or claim 2, wherein the vessel for holding the emulsion is equipped with stirring means for stirring the emulsion.

11. The apparatus according to claim 1, wherein the circulation pathway returns the aqueous portion back to the vessel after the portion has passed through the gas separation membrane module.

* * * * *